United States Patent
Carroll

(10) Patent No.: US 8,346,367 B2
(45) Date of Patent: Jan. 1, 2013

(54) APPARATUS AND METHOD FOR STABILIZING, IMPROVING MOBILITY, AND CONTROLLING CARTILAGE MATRIX DEGRADATION OF WEIGHT-BEARING ARTICULAR JOINTS

(75) Inventor: William J. Carroll, La Center, WA (US)

(73) Assignee: Meagan Medical, Inc., Vancouver, WA (US)

( * ) Notice: Subject to any disclaimer, the term of this patent is extended or adjusted under 35 U.S.C. 154(b) by 3 days.

(21) Appl. No.: 13/168,518

(22) Filed: Jun. 24, 2011

(65) Prior Publication Data
US 2011/0295339 A1      Dec. 1, 2011

Related U.S. Application Data

(63) Continuation-in-part of application No. 12/016,914, filed on Jan. 18, 2008, now Pat. No. 8,060,210, which is a continuation-in-part of application No. 10/659,278, filed on Sep. 11, 2003, now abandoned, application No. 13/168,518, which is a continuation-in-part of application No. 11/500,907, filed on Aug. 9, 2006, now abandoned.

(60) Provisional application No. 60/706,445, filed on Aug. 9, 2005, provisional application No. 60/409,589, filed on Sep. 11, 2002.

(51) Int. Cl.
*A61N 1/00* (2006.01)
(52) U.S. Cl. ......................................................... 607/48
(58) Field of Classification Search ...................... 607/48
See application file for complete search history.

(56) References Cited

U.S. PATENT DOCUMENTS
3,083,712 A      4/1963   Keegan
(Continued)

FOREIGN PATENT DOCUMENTS
JP         2000126312 A      5/2000
(Continued)

OTHER PUBLICATIONS

Fowler et al., "An Evaluation of the Analgesic Effects of Meloxicam in Addition to Epidural Morphine/Mepivacaine in Dogs Ungergoing Cranial Cruciate Ligament Repair," Can. Vet. J., vol. 44, Aug. 2003, pp. 643-648.

(Continued)

*Primary Examiner* — George Manuel
(74) *Attorney, Agent, or Firm* — Blank Rome LLP

(57) ABSTRACT

An apparatus and method for improving mobility and/or the quality of synovial fluid of an affected articular joint are disclosed, wherein the joint is associated with at least a first muscle group and at least a second muscle group each having an antagonistic relationship for effecting mobility of the joint through a range of motion when recruited by natural neural impulses. The apparatus and method include an electro-medical device configured to apply motor-level electrical stimulation in a multiphasic pattern via at least a first channel and at least a second channel, the multiphasic pattern being programmed into the electro-medical device and corresponding to the sequence of an electromyographic output for the joint; at least two first electrodes connected to the at least first channel of said electro-medical device, the at least two first electrodes being positioned proximate to the at least first muscle group; at least two second electrodes connected to the at least second channel of said electro-medical device, the at least two second electrodes being positioned proximate to the at least second muscle group; and an applicator configured to be worn on the articular segment such that the at least two first electrodes and the at least two second electrodes are disposed between the applicator and the articular segment, the applicator being further configured to reduce compressive forces on at least one compartment of the affected joint.

26 Claims, 8 Drawing Sheets

U.S. PATENT DOCUMENTS

| | | | |
|---|---|---|---|
| 3,881,494 A | 5/1975 | Paul, Jr. | |
| 3,902,502 A | 9/1975 | Liss et al. | |
| 4,165,750 A | 8/1979 | Aleev et al. | |
| 4,669,477 A | 6/1987 | Ober | |
| 4,724,842 A | 2/1988 | Charters | |
| 4,738,250 A | 4/1988 | Fulkerson et al. | |
| 4,785,813 A | 11/1988 | Petrofsky | |
| 4,976,264 A | 12/1990 | Petrofsky | |
| 5,070,873 A | 12/1991 | Graupe et al. | |
| 5,133,341 A | 7/1992 | Singer et al. | |
| 5,269,304 A | 12/1993 | Matthews | |
| 5,273,033 A | 12/1993 | Hoffman | |
| 5,324,317 A | 6/1994 | Reiss | |
| 5,350,415 A | 9/1994 | Cywinski | |
| 5,387,231 A | 2/1995 | Sporer | |
| 5,397,338 A | 3/1995 | Grey et al. | |
| 5,458,565 A | 10/1995 | Tillinghast, III et al. | |
| 5,540,735 A | 7/1996 | Wingrove | |
| 5,549,656 A | 8/1996 | Reiss | |
| 5,562,718 A | 10/1996 | Palermo | |
| 5,755,745 A | 5/1998 | McGraw et al. | |
| 5,817,138 A | 10/1998 | Suzuki | |
| 5,836,995 A | 11/1998 | MGraw et al. | |
| 5,851,223 A | 12/1998 | Liss et al. | |
| 5,947,913 A | 9/1999 | Palumbo | |
| 5,947,914 A | 9/1999 | Augustine | |
| 5,976,063 A | 11/1999 | Joutras et al. | |
| 5,980,435 A | 11/1999 | Joutras et al. | |
| 6,064,912 A * | 5/2000 | Kenney | 607/48 |
| 6,393,328 B1 | 5/2002 | McGraw et al. | |
| 6,456,884 B1 | 9/2002 | Kenney | |
| 6,456,885 B1 | 9/2002 | Shiba et al. | |
| 6,564,103 B2 | 5/2003 | Fischer et al. | |
| 6,623,454 B1 | 9/2003 | Eggers et al. | |
| 6,647,296 B2 | 11/2003 | Fischell et al. | |
| 6,725,094 B2 | 4/2004 | Saberski | |
| 6,988,005 B2 | 1/2006 | McGraw et al. | |
| 7,035,691 B2 | 4/2006 | Campos | |
| 7,257,448 B2 | 8/2007 | Crowe et al. | |
| 7,468,264 B2 | 12/2008 | Brighton et al. | |
| 7,783,348 B2 | 8/2010 | Gill et al. | |
| 2003/0135129 A1 | 7/2003 | Cusimano et al. | |
| 2004/0015207 A1 | 1/2004 | Barriskill et al. | |
| 2004/0054379 A1 | 3/2004 | Carroll et al. | |
| 2005/0010264 A1 | 1/2005 | Brighton et al. | |
| 2006/0135900 A1 | 6/2006 | Ingimundarson et al. | |
| 2007/0197946 A1 | 8/2007 | Gilmour | |
| 2008/0208287 A1 | 8/2008 | Palermo et al. | |
| 2009/0319003 A1 | 12/2009 | Castel et al. | |

FOREIGN PATENT DOCUMENTS

| | | | |
|---|---|---|---|
| JP | 2001005601 A | 1/2001 | |
| JP | 2002514108 T | 5/2002 | |
| JP | 2002191707 A | 7/2002 | |
| JP | 2002200104 A | 7/2002 | |
| WO | 9843560 A1 | 10/1998 | |
| WO | 0103768 A1 | 1/2001 | |
| WO | 2004023975 A2 | 3/2004 | |
| WO | 2005087148 A1 | 9/2005 | |
| WO | 2007019569 A2 | 2/2007 | |

OTHER PUBLICATIONS

Hua Gu, "Direct Electric Acupuncture for Patella Chondromalacia: A Preliminary Report of a Clinical Study," Acupuncture Today, Oct. 2001, vol. 2, Issue 10.

Katayama Y. "Deep Brain Stimulation Therapy for Involuntary Movements," Rinsho Shinkeigaku, vol. 41, No. 12, Dec. 1, 2001, pp. 1079-1080.

Benabid et al., "Deep Brain Stimulation of the Corpus Luysi (Subthalamic Nucleus) and Other Targets in Parkinkson's Desease. Extension to New Indications Such as Dystonia and Epilepsy," J. Neurol., Sep. 1, 2001, 248 Supp. 3: III 37-47, 2 pages.

Allert et al., "Effects of Bilateral Pallidal or Subthalamic Stimulation on Gait in Advanced Parkinson's Disease," Mov. Disord., Nov. 1, 2001, 16(6): 1076-85, 2 pages.

Utti et al., "Extended Follow-up of Unilateral Deep Brain Stimulation for Tremor," P03.113; A220-221, 1 page.

Obwegeser et al., "Quantitative and Qualitative Outcome Measures After Thalamic Deep Brain Stimulation to Treat Disabling Tremors," Neurosurgery, 48(2); Discussion 281-4, 2001, 2 pages.

Obwegeser et al., "Simultaneous Thalamic Deep Brain Stimulation and Implantable Cardioverter-Defbrilator," Mayo. Clin. Proc., 76(1): 78-9, 2001, 2 pages.

Obwegesser et al., "Thalamic Stimulation for the Treatment of Midline Tremors in Essential Tremor Patients," Neurology, 54(12): 2342-4, 2000, 2 pages.

Oh et al., "Deep Brain Stimulator Electrodes Used for Lesioning: Proof of Principle," Neurosurgery, Aug. 1, 2001, 49(2): 363-7, Discussion 367-9, 2 pages.

Racette et al., "Thalamic Stimulation for Primary Writing Tremor," J. Neurol., May 1, 2001, 248(5):380-2, 2 pages.

Rocchi et al., "Effects of Deep Brain Stimulation and Levodopa on Postural Sway in Parkinson's Disease," J. Neurol. Neurosurg. Psychiatry, Sep. 2002, 73(3):267-74, 2 pages.

Nasser et al., "Deep Brain Stimulation of VIM Thalamic Nucleus for Tremor Control," Arq. Neuropsiquiatr., Jun. 2002, 60(2-B):429-34, 1 page.

Racette et al., "Ipsilateral Thalamic Stimulation After Thalamotomy for Essential Tremor. A Case Report.," Stereotact Funct. Neurosurg. Jan. 1, 2000, 75(4):155-9; 2 pages.

Maya Pines,"New Imaging Techniques That Show the Brain at Work: Brain Scans That Spy on the Senses," Seeing, Hearing, and Smelling the World, A Report from the Howard Hughes Medical Institute, 2 pages.

Maya Pines, "New Imaging Techniques that Show the Brain at Work: The Next Generation of Brain Scans," Seeing, Hearing, and Smelling the World, A Report from the Howard Hughes Medical Institute, 2 pages.

Oregon Imaging Article, "P.E.T. Scan—Patient Information," 2 pages, www.oregonimaging.com/patient/petinfo.com.

Cigna Corporation, "Positron Emission Tomography (PET) Scans—Medicare Coverage," All States, GR 99-4, Jul./Aug. 1999, 7 pages.

Rezai et al., "Neurostimulation Systems for Deep Brain Stimulation: in Vitro Evaluation of Magnetic Resonance Imaging-Related Heating at 1.5 Tesla," J. Magn. Reson. Imaging, Mar. 1, 2002, 15(3):241-50, 2 pages.

Mobile PET Systems, Inc. "Clinical Applications," 5 pages.

Neurological Associates, Inc. "Deep Brain Stimulation," 6 pages, www.wvneuro.com/deep%20brain%20stimulation.htm.

Hamza et al., "Effect of the Duration of Electrical Stimulation on the Analgesic Response in Patients with Low Back Pain," Anesthesiology, Dec. 1999, vol. 91, No. 6, pp. 1622-1627.

Ghoname et al., "The Effect of Stimulus Frequency on the Analgesic Response to Percutaneous Electrical Nerve Stimulation in Patients with Chronic Low Back Pain," Anesthesia & Analgesia, vol. 88, No. 4, Apr. 1999, pp. 841-846.

Seroussui et al., "Effectiveness of Percutaneous Neuromodulation Therapy for Patients with Chronic and Severe Low Back Pain," Pain Practice, vol. 3, Issue 1, 2003, pp. 22-30.

Ghoname et al., "Percutaneous Electrical Nerve Stimulation for Low Back Pain," JAMA, vol. 281, No. 9, Mar. 3, 1999, pp. 818-823.

Robinson et al., "Clinical Elecrophysiology, Electrotherapy and Electrophysiologic Testing," Second Edition, Williams & Wilkins, pp. cover, 285, 288-290.

Johnson et al., "An In-Depth Study of Long-Term Users of Transcutaneous Electrical Nerve Stimulation (TENS). Implications for Clinical Use of TENS.," Pain, vol. 41, 1991, pp. 221-229.

Han et al., "Effect of Low-and High-Frequency TENS on Met-Enkephalin-Arg-Phe and dynorphin A Immunoreactivity in Human Lumbar CSF," Pain, vol. 47, 1991, pp. 295-298.

Nelson et al., Editors, "Clinical Electrotherapy," third edition, Appelton & Lange, Stamford, Connecticut, pp. cover, 316-319.

Peer Review Network, Inc., "Special Report: Vertis Percutaneous Neuromodulation Therapy (PNT)," PRN Newsletter, vol. 9, No. 6, Nov. 2002, pp. 1-5.

Gopalkrishnan et al., "Effect of Varying Frequency, Intensity, and Pulse Duration of Transcutaneous Electrical Nerve Stimulation on Primary Hyperalgesia in Inflamed Rats," Arch. Phys. Med. Rehabil., vol. 820, Jul. 2000, pp. 984-990.

Johnson et al., "Analgesic Effects of Different Frequencies of Transcutaneous Electrical Nerve Stimulation on Cold-Induced Pain in Normal Subjects," Pain, vol. 39, 1989, pp. 231-236.

Marchand et al., "Modulation of Heat Pain Perception by High Frequency Transcutaneous Electrical Nerve Stimulation (TENS)," The Clinical Journal of Pain, vol. 7, 1991, pp. 122-129.

Wise C (1999). Osteoarthritis. In DC Dale, DD Federman, eds., Scientific American Medicine, vol. 1, part 1, chap. 15, pp. 1-7. New York: Scientific American.

Baker L (1993). Applications of NMES with Traditional Treatment Programs. NeuroMuscular Electrical Stimulation A Practical Guide 3rd ed., pp. 169-185. Downey: Los Amigos research & Education Institute, Inc.

Cooper C, Coggon D (1999). Physical activity and knee Osteoarthritis. Lancet 353(9171): 2177-2178.

Dieppe P, et al. (2000). Osteoarthritis. Clinical Evidence, 3: 529-541.

Lane NE, Thompson JM (1997). Management of Osteoarthritis in the primary-care setting: An evidence-based approach to treatment. American Journal of Medicine, 103 (6A): 25S-30S.

\* cited by examiner

APPARATUS AND METHOD FOR STABILIZING, IMPROVING MOBILITY, AND CONTROLLING CARTILAGE MATRIX DEGRADATION OF WEIGHT-BEARING ARTICULAR JOINTS

CROSS REFERENCE TO RELATED APPLICATIONS

The present application is a continuation-in-part of co-pending U.S. application Ser. No. 12/016,914, filed Jan. 18, 2008, which is a continuation-in-part of U.S. application Ser. No. 10/659,278, filed Sep. 11, 2003 (hereinafter "the '278 application"), abandoned, and is also a continuation-in-part of co-pending U.S. application Ser. No. 11/500,907, filed Aug. 9, 2006 (hereinafter "the '907 application). The '278 application claims the benefit of U.S. Provisional Application No. 60/409,589, filed Sep. 11, 2002, and the '907 application claims the benefit of U.S. Provisional Application No. 60/706,445, filed Aug. 9, 2005. The disclosures of those applications are hereby incorporated in their entirety by reference as if fully set forth herein.

FIELD OF THE INVENTION

The present invention generally relates to degenerative joint disease and osteoarthritis and, more particularly, is related to an apparatus and method for stabilizing, improving mobility, and controlling cartilage matrix degradation of weight-bearing articular joints.

BACKGROUND OF THE RELATED ART

Historically, electrical muscle stimulation has been employed to re-educate and re-train impaired muscles. The restoration of movement, especially in stroke paralysis, has seen limited success with what is known as functional electrical stimulation (i.e., electrical stimulation that actually causes an articular segment to move, or articulate, through its full range of motion). The goal of functional electrical muscle stimulation is to restore functional capacity of muscles following a debilitating trauma. Primary candidates for functional electrical muscle stimulation include persons with paraplegia, hemiplegia and quadriplegia, as well as individuals with spinal cord injury or patients suffering from an impairment of the central nervous system, e.g., multiple sclerosis, head injury, or cerebral palsy.

U.S. Pat. No. 3,083,712 to Keegan (hereinafter "Keegan") relates generally to electrical muscle therapy and, more specifically, to a programmed sequence for muscle therapy. It is an object of Keegan to provide an apparatus for producing sequential programming between antagonistic muscles in a proper time relation required for normal function of the muscles. In the illustrative example of Keegan, stimulation through an electrode is applied to the peroneal nerve, which causes muscle dorsiflexion and a slight eversion (i.e., turning out) of the foot. In that example, the electrical stimulation is provided to assure that the toes of a foot will be lifted while the foot is being swung forward to avoid the dragging of the toes, dragging the toes being at the paralyzed side of the body while walking being characteristic of hemiplegics. The electrical stimulation of that example is provided when a switch is depressed as the heel strikes the ground, thereby bridging contacts to provide energy from a battery source. Accordingly, the "sequential programming" of Keegan relates to a method for stimulating the peroneal nerve when a switch is depressed, not stimulating multiple muscles in a sequence. The functional movements caused, if at all, by that type of stimulation rarely become voluntary movements for the patient.

The ultimate goal for patients with spinal cord injury is to ambulate. Accordingly, muscles may be stimulated in the swing phase by electrical stimulation to advance the articular segment through its range of motion. Muscles are also stimulated during the stance phase so the patient can remain in the upright position. Despite the presence of momentary recovery periods between the swing and stance phases of an articular segment, fatigue sets in rapidly and muscles can simply fail due to the electrical stimulation's activation of fatigue-prone fast motor units. Fatigue may also prevail because disruptions of the spinal cord promote the conversion of slow fatigue-resistant to fast-fatigable muscle fibers, particularly in the weight-bearing muscles that cross articular joints. Further, postural instability during such stimulation may cause falls. That instability is related to the small number of muscles stimulated by such electrical stimulation as compared to the total number of muscles that would normally require stimulation to cause the articular segment to move through its full range of motion.

Accordingly, attempts have been made to overcome muscle failure due to fatigability and due to conversion of slow-twitch to fast-twitch muscle while a limb advances through its range of motion. U.S. Pat. No. 4,165,750 to Aleev et al. (hereinafter "Aleev") relates to a bioelectrically controlled electric stimulator of human muscles comprising an oscillator and a group of stimulator channels. Aleev uses a live person and functional electrical stimulation to improve the correspondence between movements actually performed by a human and programmed movements to mitigate pain in the course of stimulation, and to make it possible to check the fatigability of muscles in the course of electrical stimulation by changing the stimulation conditions at the onset of fatigability. Aleev attempts to achieve those objects in a system that senses the bioelectric activity of the muscles of a programmer, manipulates the corresponding electric signal, and applies it to the muscles of a person whose movements are under control, all while continuing to sense the bioelectric activity of the muscles of the programmer, who may be a different person than the person whose movements are under control. Those objects are meant not only to restore the strength of damaged muscles, but also to restore lost motor skills (i.e. to enable a person to perform compound motions of the extremities, torso and head similar to those of a healthy person's extremities, torso, and head).

U.S. Pat. No. 5,350,415 to Cywinski (hereinafter "Cywinski") relates to a device for trophic stimulation of muscles that does not depend on muscle contraction to achieve a therapeutic result. The device of Cywinski contains a pulse generation circuit that mimics the motor unit action potentials (MUAPs) that are naturally generated when muscles are innervated. MUAPs are known to have a mean rate of firing between 5 and 15 pulses per second, which is far below the stimulation rate necessary to achieve fused and forceful contraction of muscle. An object of Cywinski is to stimulate a trophic change of muscle contractile properties from fast-fatiguing into slow fatigue resistant types. Accordingly, Cwyinski achieves that therapeutic result without causing fused and forceful contraction of a muscle.

Electrical stimulation can be patterned after the body's natural movements and is hereinafter referred to as "patterned electrical muscle stimulation." Patterned electrical muscle stimulation applies a template of the firing pattern recorded in a healthy articular segment as it moves through its full range of motion. Patterned electrical muscle stimulation may also be patterned after the body's natural MUAPs or any other observable sequencing of muscles. For example, the intact biceps and the triceps muscles' activity pattern may be detected in the form of electromyographic output and recorded during the flexion of the straight arm. Then, the timing and amplitude parameters of those electromyographic activities (i.e., the synergy patterns) are analyzed. Using a mathematical model, the activity patterns are reconstructed and applied via an electrical muscle stimulator to the impaired muscle pair. When impaired muscles contract, a sensory stimulus pattern ascends to the brain where, in a way thus far unidentified, a new motor template is generated. Once the new motor template is available, voluntary functional movement may become possible.

The methods discussed above relate primarily to the treatment of impaired muscles. More recently, researchers have studied the physiological processes for bioelectrical interactions among, and the activity regarding the growth and repair of, certain tissues and cells other than muscles. For example, osteoarthritis, also known as degenerative joint disease, is characterized by degeneration of articular cartilage, as well as proliferation and remodeling of subchondral bone. The usual symptoms of osteoarthritis are stiffness, limitation of motion, and pain. Osteoarthritis most commonly affects the knee joint more so than any other articular joint. Articular joints are encapsulated in a protective sac-like structure called a bursa, and there is a lining of the joint called the synovium that produces synovial fluid. This synovial fluid bathes and lubricates the articular surfaces of the joints and helps protect the cartilage. Synoviocytes and other cells found in the joint spaces adjacent to cartilage also have an important role in cartilage metabolism (e.g., synoviocytes produce metalloproteinases that are capable of breaking-down cartilage).

The breakdown of cartilage that is seen in conditions of osteoarthritis occurs in several stages. First, the synovial fluid becomes thinner and loses its elasticity and viscosity, which decreases its ability to cushion the joint. Without this cushioning effect, the cartilage in the joint may be more likely to "wear down." Therefore, the surface of the smooth cartilage covering the joint softens and begins to lose its ability to absorb the impact of movement and can be more easily damaged from excess use or shock. The joint may also lose its shape as the cartilage breaks down, and bony growth or bone spurs may form on the edges of the affected joint compartment. As a result, small particles of bone and cartilage may degrade and begin to float around in the joint space, which contributes to the further degradation of the affected joint. Thus, one factor for measuring the effectiveness of methods of treatment for osteoarthritis may be the quantitative and qualitative analyses for measuring the viscosity and density of synovial fluid.

A typical standard of care for treating osteoarthritis is bracing the affected joint. Typical braces relieve pain by reducing the compressive forces on the joint being braced. For example, U.S. Pat. No. 5,458,565 to Tillinghast, III (hereinafter "Tillinghast") relates to an osteoarthritic knee brace having flexible upper and lower arm members rotatably connected to each other by a rotary hinge assembly and an inflatable or deflatable fluid-containing pad positioned between the hinge assembly and the knee joint, and U.S. Published Patent Application No. 2006/0135900 to Ingimundarson et al. (hereinafter "Ingimundarson") relates to an osteoarthritic knee brace having a flexible proximal shell and a flexible distal shell. The embodiments of Tillinghast are directed to the object of stabilizing an osteoarthritic knee joint and reducing the pain of the user by distributing a radially directed treatment force across the pad to the surface of the knee joint engaging the pad. And the embodiments of Ingimundarson are directed to the object of reducing the effects of compartmental osteoarthritis by applying multiple forces to the knee on the side remote from the compartment having osteoarthritis while providing forces on the side of the compartment to maintain the brace securely on a leg while minimizing rotational forces.

Although such knee braces have been used with varying levels of effectiveness to treat osteoarthritis, none have been successfully combined with electrical stimulation that controls cartilage matrix degradation. For example, U.S. Pat. No. 6,456,885 to Shiba et al. (hereinafter "Shiba") relates to a muscle strengthening knee brace combined with electrical stimulation that is provided to an antagonist muscle when the corresponding agonist muscle is in a contracting state. That electrical stimulation is used to generate resistance as a patient tries to straighten or bend an articular segment during a closed-kinetic-chain exercise. And the resulting muscle contractions subject the bone surrounded by those muscles to axial compressive loading. Such loading, however, runs contrary to the forces that Tillinghast and Ingimundarson seek to minimize.

As set forth in the discussion above, there remains a need in the art for an apparatus and method for stabilizing, improving mobility, and controlling cartilage matrix degradation of weight-bearing articular joints. More particularly, there remains a need in the art for an apparatus and method that allows patients greater mobility with relief of osteoarthritis symptoms while simultaneously allowing the symptoms to be treated.

SUMMARY OF THE INVENTION

Accordingly, it is an object of the invention to provide an apparatus and method for stabilizing, improving mobility, and controlling cartilage matrix degradation of weight-bearing articular joints. The apparatus and method include an electro-medical device configured to apply motor-level electrical stimulation in a multiphasic pattern via at least a first channel and at least a second channel, the multiphasic pattern being programmed into the electro-medical device and corresponding to the sequence of an electromyographic output for the joint; at least two first electrodes connected to the at least first channel of said electro-medical device, the at least two first electrodes being positioned proximate to the at least first muscle group; at least two second electrodes connected to the at least second channel of said electro-medical device, the at least two second electrodes being positioned proximate to the at least second muscle group; and an applicator configured to be worn on the articular segment such that the at least two first electrodes and the at least two second electrodes are disposed between the applicator and the articular segment, the applicator being further configured to reduce compressive forces on at least one compartment of the affected joint. Those and other objects, advantages, and features of the present invention will become more readily apparent by the following written description, taken in conjunction with the accompanying drawings and claims.

BRIEF DESCRIPTION OF THE DRAWINGS

Many aspects of the present invention can be better understood with reference to the accompanying drawings, which are part of the specification and represent exemplary embodiments of the present invention.

The components in those drawings are not necessarily to scale, emphasis instead being placed upon clearly illustrating the principles of the present invention. Also in those drawings, like reference numerals designate corresponding parts throughout the several views.

DETAILED DESCRIPTION OF THE PREFERRED EMBODIMENTS

Figure 1:
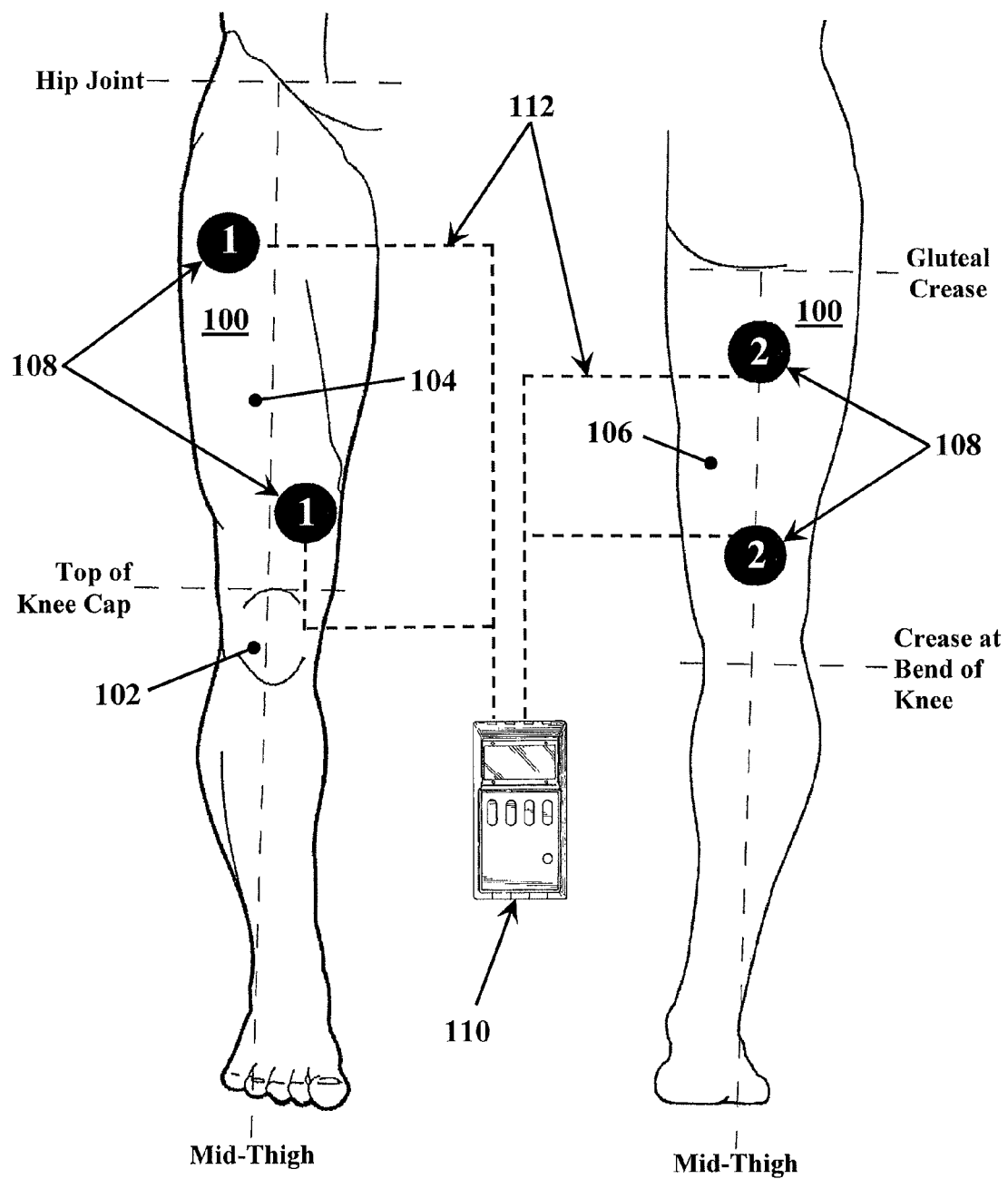
FIG. 1 is a front-side and back-side view of a weight-bearing articular segment illustrating the placement of surface skin electrodes to promote motor-level electrical stimulation in a triphasic pattern based on an electromyographic output for stimulating the antagonistic muscle groups associated with the joint.

The present invention overcomes the shortcomings of the prior art and provides at least the advantages discussed below by utilizing patterned electrical muscle stimulation in combination with a stabilizer to improve mobility of and to control cartilage matrix degradation in affected, weight-bearing, articular joints. Those and other advantages provided by the present invention can be better understood from the description of the preferred embodiments below and in the accompanying drawings. In describing the preferred embodiments, specific terminology is resorted to for the sake of clarity. However, the present invention is not intended to be limited to the specific terminology so selected, and it is to be understood that each specific term includes all technical equivalents that operate in a similar manner to accomplish a similar purpose. For example, although the preferred embodiments are directed to an articular segment that is a leg and a joint that is a knee, it is also contemplated that the present invention may be used for electrically stimulating and stabilizing other articular segments with joints including, but not limited to, elbows, ankles, shoulders, hips, toe joints, and finger joints.

A. Apparatus

Turning to the drawings, reference character 100 identifies an articular segment 100 with an affected, weight-bearing, joint 102. Motor-level patterned muscle electrical stimulation is applied to the muscle groups 104 and 106 that produce movement, or articulation, of the joint 102 via four surface skin electrodes 108 and an electro-medical device 110. That patterned muscle stimulation causes fused and forceful contraction of muscle groups 104 and 106 in a sequence that mimics normal joint action without actually causing the articular segment 100 to move through the range of motion associated with normal joint action. That sequence of muscle contraction subjects the joint 102 to conditions that naturally enhance vegetative function without incurring weight-bearing load.

FIG. 1 illustrates an apparatus and method for improving mobility of and controlling cartilage matrix degradation of an affected joint 102, specifically a knee joint 102, by applying motor-level patterned muscle electrical stimulation using surface skin electrodes 108. The surface skin electrodes 108 may be placed at predetermined locations on the articular segment 100 such that the electrical stimulation pattern corresponds to the sequence of electrical discharges in individual muscle cells of the muscle groups 104 and 106 that contract together in a pattern to perform compound motions during natural movements of a non-affected knee joint 102.

Figure 2:
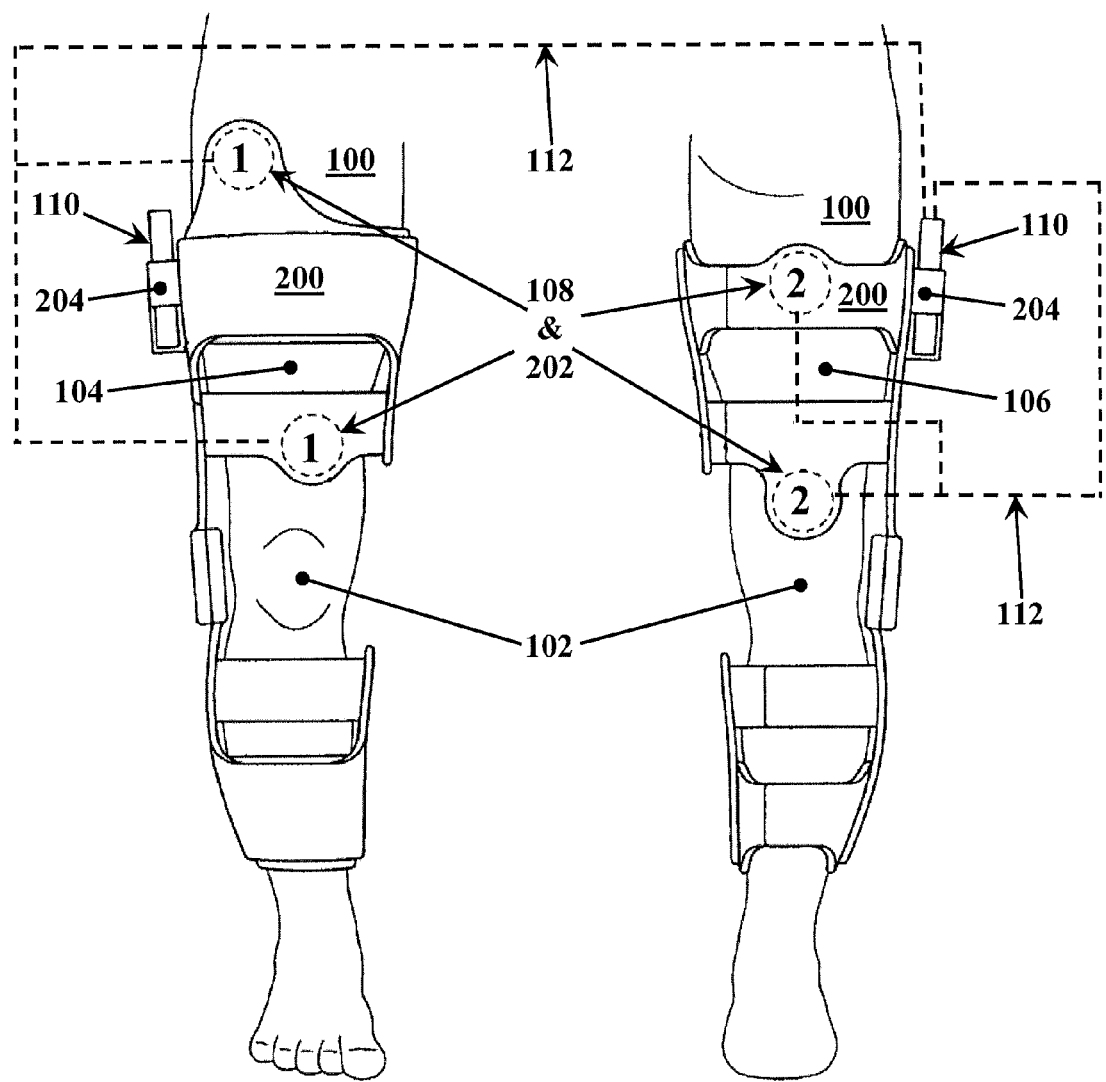
FIG. 2 is a front-side and back-side view of a weight-bearing articular segment illustrating the placement of surface skin electrodes with a stabilizer.

FIG. 2 illustrates an apparatus and method for improving mobility of and controlling cartilage matrix degradation of an affected joint 102, specifically a knee joint 102, by applying motor-level patterned muscle electrical stimulation using surface skin electrodes 108 disposed in a stabilizer 200. Because the surface skin electrodes 108 may be placed at predetermined locations on the articular segment 100, the stabilizer 200 may include attachment portions, or pockets, 202 where the surface skin electrodes 108 can be attached to, or installed in, the stabilizer 200 at locations that correspond to predetermined locations on the articular segment 100 when the stabilizer 200 is worn on the articular segment 100. In that manner, the surface skin electrodes 108 can be easily and repeatably positioned at the predetermined locations on the articular segment 100 whenever a patient wears the stabilizer 200.

In FIGS. 1 and 2, the surface skin electrodes 108 are placed on a muscle group 104 on the front area of the thigh and a muscle group 106 on the back area of the thigh. More specifically, on the front area of the thigh, one surface skin electrode 108 is placed over the vastus lateralis and one surface skin electrode 108 is placed over the vastus medialis, wherein those two muscles make up the muscle group 104, or the quadriceps, on the front area of the thigh. On the back area of the thigh, one surface skin electrode 108 is placed over the proximal biceps femoris and one surface skin electrode 108 is placed over the distal biceps femoris, wherein those two muscles make up the muscle group 106, or the hamstrings (generally), on the front area of the thigh.

Also in FIGS. 1 and 2, the surface skin electrodes 108 are connected to an electro-medical device 110 that is configured to supply electrical stimulation signals to the muscle groups 104 and 106 using multiple channels. Those connections are made via electrical conductors, or leads, 112 that extend between the surface skin electrodes 108 and the electro-medical device 110. The pair of surface skin electrodes 108 placed on the muscle group 104 on the front area of the thigh correspond to Channel 1 of the electro-medical device 110, and the pair of surface skin electrodes 108 placed on the muscle group 106 on the back area of the thigh correspond to Channel 2 of the electro-medical device 110. The electro-medical device is adapted to provide multiple types and levels of stimulation through each of its four channels. An example of such an electro-medical device 110 is the portable muscle stimulator disclosed in U.S. Pat. Nos. 6,393,328 and 6,988,005 to McGraw et al., the disclosures of which are hereby incorporated by reference as if fully set forth herein.

Figure 3:
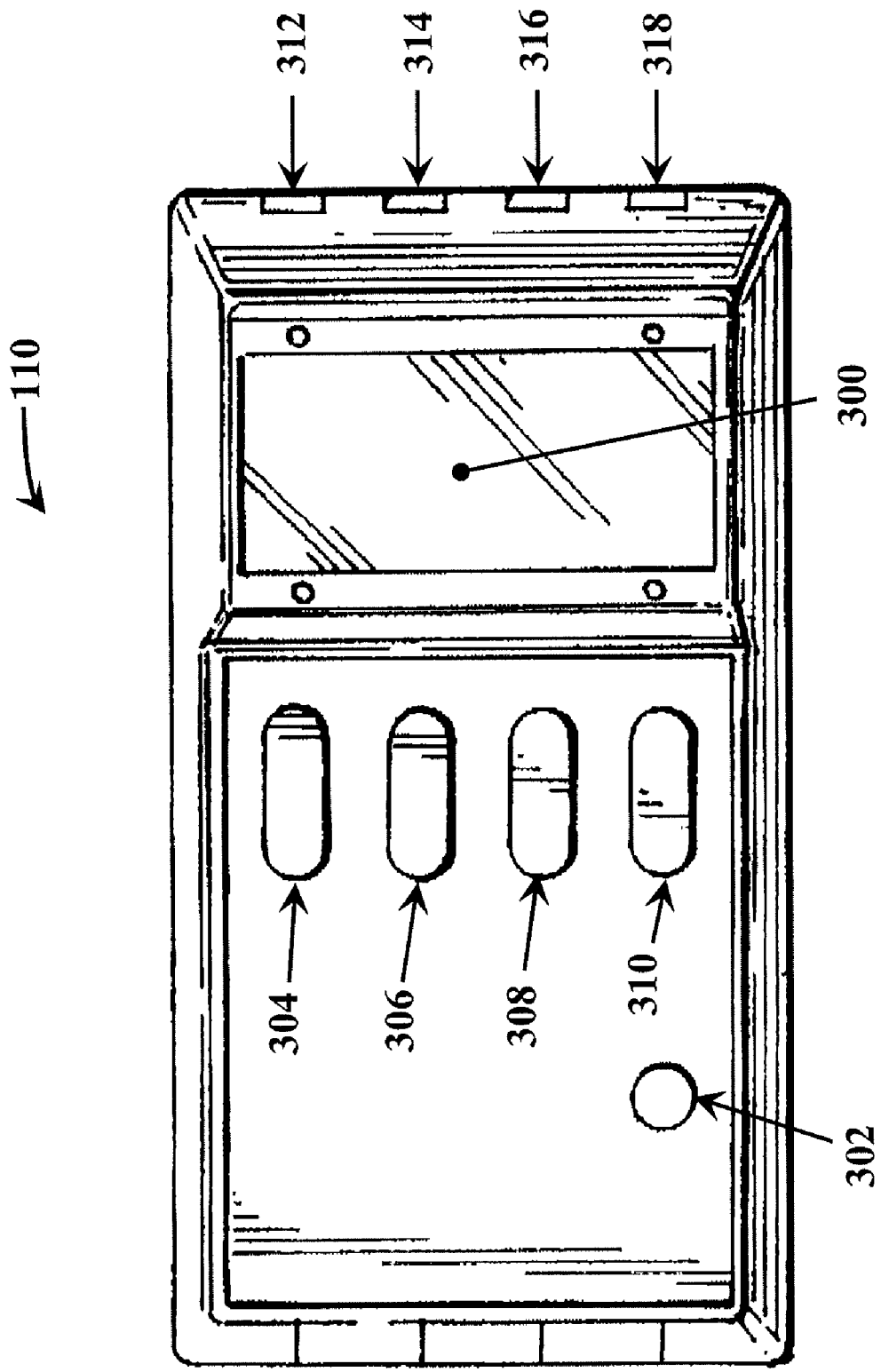
FIG. 3 is a top view of an exemplary embodiment of an electro-medical device of the present invention.

FIG. 3 illustrates an exemplary embodiment of such a portable muscle stimulator. As shown in FIG. 3, the electro-medical device 110 includes a liquid crystal display (LCD) 300 to provide visual feedback and an interface for the user to determine the type, level, and length of electrical stimulation treatment. The electro-medical device 110 also includes a power switch 302 and four switches 304-310 for controlling the respective outputs of each of four isolated channels contained in the electro-medical device 110. Four output jacks 312-318 are provided at the front of the electro-medical device 110 with a separate jack being provided for each of up to four electrically isolated output channels that are capable of independently treating four separate muscle groups. Each of the electrically isolated channels may have a separate intensity control (e.g., switches 304-310) for independently increasing and decreasing the intensity of stimulation provided by that channel. Accordingly, the surface skin electrodes 108 are in electrical communication with the electro-medical device 110 via electrically separate leads 112 that are plugged into the output jacks 312-318, wherein each pair of surface skin electrodes 108 is connected to a single output jack 312-318. Additionally, the electro-medical device 110 may be provided with a programmable data storage card that is configured with usage monitoring functionality so that it can be easily and safely used by an unsupervised patient, such as the data card disclosed by in U.S. Pat. Nos. 5,836,995 and 5,755,745 to McGraw et al., the disclosures of which are hereby incorporated by reference as if fully set forth herein.

Returning to FIG. 2, the surface skin electrodes 108 are mounted in the stabilizer 200 at the attachment portions 202 such that they are positioned between the stabilizer 200 and the articular segment 100 at the inner surface, or skin-side surface, of the stabilizer 200. Each attachment portion 202 includes an electrical contact (not shown) for making an electrical connection between each surface skin electrode 108 and its corresponding lead 112. A portion of those leads 112 may be hard wired within the stabilizer 200 and include connection points at an outer surface of the stabilizer 200 where they can be quickly and conveniently connected to the remaining portions of the leads 112 or directly to the output jacks 312-318 of the electro-medical device 110. In FIG. 2, for example, the stabilizer 200 includes a dock 204 that is configured to receive the electro-medical device 110 therein and to directly connect the output jacks 312-318 of the electro-medical device 110 to leads 212 that are hard wired within the stabilizer 200. The dock 204 is preferably disposed on the stabilizer 200 in a location that prevents it from interfering with a patient's movement, such as on the side of the stabilizer 200 facing away from an opposing articular segment 100.

The surface skin electrodes 108 are preferably double-sided, or double-stick, that adhesively attach to both the inner surface of the stabilizer 200 and the skin of the articular segment 100 when the stabilizer 200 is worn by a patient. The surface skin electrodes 108 are also preferably reusable, disposable, and replaceable so they can be removed from the stabilizer 200 without disrupting the connectivity with the electrical contacts that electrically connect the surface skin electrodes 108 to the leads 112. And the surface skin electrodes 108 are preferably repositionable within the stabilizer 200 so as to accommodate different patients with different sized and shaped articular segments 100 as well as to accommodate different electrode configurations. The surface skin electrodes 108 can be made repositionable within the stabilizer 200 by disposing the attachment portions 202 and their corresponding electrical contacts in adjustable straps.

The stabilizer 200 is configured to reduce the compressive forces on at least one compartment of the affected joint 102. In a leg 100, for example, the medial compartment of the knee joint 102 is usually effected more than the lateral compartment. Accordingly, a single-hinge stabilizer 200 can be used to provide lateral forces that oppose the pathologically unbalanced load within the medial compartment of the knee joint 102. The stabilizer 200 thereby removes weight bearing stress from the osteoarthritic or otherwise affected compartment of the knee joint 102 and transfers it onto the healthy compartment. The reduction of compressive forces on the medial compartment of the knee joint 102 results in less pain and wear of the knee joint 102. Thus, the stabilizer 200 of the present invention can be combined with electrical muscle stimulation to improve the mobility of and to control cartilage matrix degradation in affected, weight-bearing, joints 102 of articular segments 100.

B. Methods

In one embodiment of the present invention, the application of the electrical stimulation occurs by employing a symmetrical waveform via pairs of surface skin electrodes 108 electrically connected to separate channels of the electro-medical device 110. The symmetry of the waveform allows the pairs of surface skin electrodes 108 for each channel to operate with anode and cathode interchangeability. Alternatively, the electrical stimulation may employ asymmetrical waveforms such that the surface skin electrodes 108 for the pairs at each channel correspond individually to an anode or a cathode, without interchangeability.

In the non-limiting configuration of FIGS. 1 and 2, the electrical stimulation may be applied to each muscle group 104 and 106 of the affected joint 102 at the "motor level", thereby causing the corresponding muscles to achieve fused and forceful contraction. In an exemplary embodiment of the present invention, the motor-level stimulation may have a parameter set that causes an action potential to be generated at a nerve or muscle of the affected joint 102. The parameter set may form a biphasic, symmetrical waveform that modulates frequency, amplitude, and/or phase to produce a period of action potentials sufficient to cause strong, visible contractions of the stimulated muscle, but without actually causing the articular segment 100 to move through its full range of motion (i.e., parameters that do not cause functional electrical stimulation).

Figure 4:
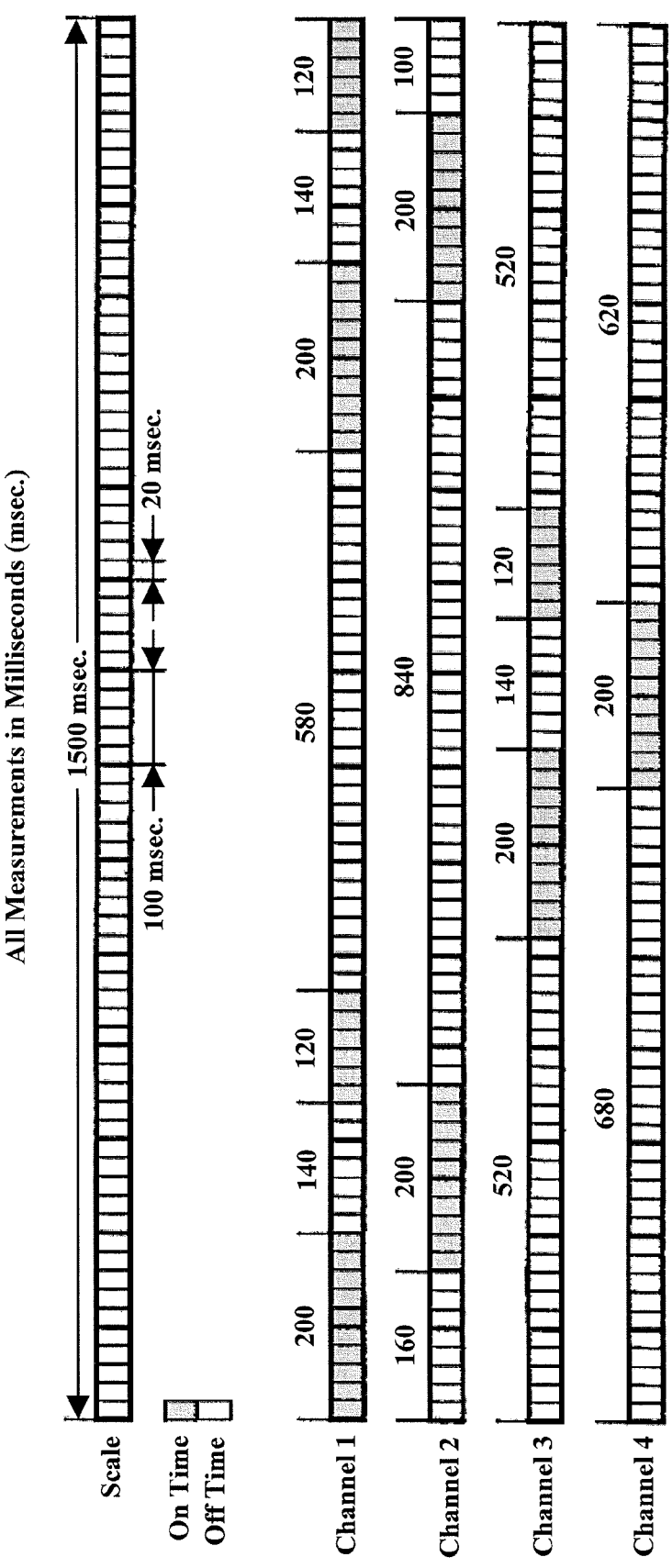
FIG. 4 illustrates the relative timing pattern of sequenced current, as applied to antagonistic muscle groups of an affected joint.

FIG. 4 is a chart that illustrates the relative timing pattern of sequenced current, as applied to antagonistic muscle groups 104 and 106 of an articular segment 100, in accordance with the motor-level patterned electrical muscle stimulation of the present invention. That chart of FIG. 4 illustrates the "on time" and "off time" for applying motor-level stimulation to each of those muscle groups 104 and 106. The "on time" corresponds to a period of applying electrical stimulation and is represented by the shaded in areas of the graph, and the "off time" corresponds to a period of not applying electrical stimulation and is represented by the areas of the graph that are not shaded.

The motor-level patterned electrical muscle stimulation of the present invention may be provided in a multi-phase, or multiphasic, pattern. In the non-limiting embodiments described hereinafter, the electrical stimulation is described with reference to a pattern that includes three phases (i.e., a triphasic pattern). As illustrated in FIG. 4, the motor-level patterned electrical muscle stimulation is provided in a triphasic pattern that includes stimulating the quadriceps 104, then the hamstring muscles 106, and back again to the quadriceps 104. The first phase of the three phase stimulation sequence causes the contraction of the quadriceps 104. As the quadriceps 104 nearly complete their contractions, the hamstring muscles 106 begin to receive electrical stimulation, thereby causing contraction of the hamstring muscles 106. There is a period of overlap between phase 1 and 2 of the three phase stimulation where both the quadriceps 104 and hamstring muscles 106 are stimulated at the same time. As the hamstring muscles 106 nearly complete their contractions, the quadriceps 104 are again stimulated. Similar to phase 1 and 2, there is a period of overlap between phase 2 and 3 of the three phase stimulation. That sequence of electrical stimulation produces the normal vegetative functions of the knee 102, such as production of synovial fluid without further degradation of the knee joint 102.

Unlike Shiba, where the electrical stimulation subjects the knee joint 102 to a compressive axial loading, the motor-level patterned electrical muscle stimulation of the present invention does not subject the knee joint 102 to any additional weight-bearing load. Also unlike Shiba, where the electrical stimulation is applied as the patient bends or straightens an articular segment 100 as part of a closed-kinetic-chain exercise, the motor-level patterned electrical muscle stimulation can achieve the desired result of improving the quality of synovial fluid in an affected joint 102 without requiring the patient to move his or her articular segment 100 through its range of motion, thereby preventing any increase in moving friction during the stimulation. Thus, the motor-level patterned electrical muscle stimulation of the present invention complements the reduction of compressive forces provided by the stabilizer 200 rather than working against it, as in Shiba.

In the sequential firing pattern illustrated in FIG. 4, the on and off times for Channels 1 and 2 correspond to the periods of electrical discharge across the quadriceps 104 and hamstring muscles 106 during normal joint action. More specifically, the firing pattern illustrated in FIG. 4 emulates the timing pattern of muscular contractions as electromyographically recorded from the quadriceps 104 and hamstring muscles 106 of a weight-bearing, articular joint 102 as it moves through its full range of motion. According to the present invention, electromyographic outputs (not shown) were recorded from live motor nerves while in a state of high-level activity (e.g., motor nerves of the quadriceps 104 and hamstring muscles measured 106 while the live subject was running). The timing pattern for which the muscle groups 104 and 106 contract was then reproduced, as shown in FIG. 4, to generate the motor-level patterned electrical muscle stimulation of the present invention. That electrical stimulation is delivered by the electro-medical device 110 in a pattern that is based on the timing of the pattern of the live motor nerves of those muscle groups 104 and 106. And as that patterned muscle stimulation is applied, the affected joint 102 is subjected to conditions that allow it to undergo vegetative functionality without actually causing the joint to move through its biologically designed range of motion.

Also in the sequential firing pattern illustrated in FIG. 4, the on and off times for Channels 1 and 2 correspond to the periods of electrical discharge across the quadriceps 104 and hamstring muscles 106 of a first leg 100, respectively, while the on and off times for Channels 3 and 4 correspond to the periods of electrical discharges across the quadriceps 104 and hamstring muscles 106 of a second leg 100. Electrical stimulation, therefore, may be applied to an affected knee joint 102 of each leg 100 at the same time using an electro-medical device 110 having at least four stimulation Channels 1-4. In that non-limiting embodiment, the surface skin electrodes 108 that correspond to Channel 1 are placed on the front area of the first leg 100; the surface skin electrodes 108 that correspond to Channel 2 are placed on the back area of the first leg 100; the surface skin electrodes 108 that correspond to Channel 3 are placed on the front area of the second leg 100; and the surface skin electrodes 108 that correspond to Channel 4 are placed on the back area of the second leg.

Applying motor-level stimulation to the muscle groups 104 and 106 associated with a specific joint 102 in a sequence that mimics an electromyographic output pattern controls cartilage matrix degradation by causing fused and forceful contractions in the muscle groups 104 and 106 associated with the affected joint 102 without causing the articular segment 100 to move through its full range of motion. Those muscle contractions promote blood flow in the joint 102 and its associated muscle groups 104 and 106 without causing grinding and friction, which are contributing factors to cartilage matrix degradation. And as discussed above, the stabilizer 200 helps prevent grinding and friction when the articular segment 100 does move through its full range of motion, such as when the patient mobilizes the articular segment 100 between treatment sessions.

The motor-level patterned electrical muscle stimulation of the present invention is preferably applied to the muscle groups 104 and 106 of an affected joint 102 while the corresponding articular segment 100 is in a position that minimizes pressure and moving friction therein, such as applying the stimulation to the knee joint 102 while the person is sitting or lying down. Such methods of treatment allow stimulation that mimics normal activities of daily living, such as walking or running, to be applied without producing the type of destructive wear and tear on the affected joint 102 that would normally occur during such activities. And when the patient does choose to engage in such activities, the stabilizer 200 will help mitigate the amount of wear and tear on the affected joint 102 to preserve the benefits of the motor-level patterned electrical stimulation. Moreover, because such stabilizers 200 are typically worn for long periods of time, particularly by physically active patients, patients can leave the surface skin electrodes 108 on the targeted muscle groups 104 and 106 between treatment sessions, thereby eliminating the need to remove and reapply the surface skin electrodes 108 before and after each treatment session.

Also in the configuration of FIGS. 1 and 2, interferential current can be delivered using the four surface skin electrodes 108 and electro-medical device 110 of the present invention. In applying a known type of interferential current called pre-modulated interferential current, the two currents are mixed in the electro-medical device 110 before being delivered to the patient's skin via the surface skin electrodes 108. In a conventional application for delivering true interferential currents, the interferential currents can be produced endogenously in the patient. But the clinical difference between the two delivery methods is not significant, if discernible at all. Accordingly, pre-modulated delivery offers an ease of application in the present invention by allowing the same electrode configuration to be used to apply both motor-level patterned electrical stimulation and interferential stimulation. Moreover, it allows both of those types of stimulation to be applied without reconfiguring the locations of the surface skin electrodes 108 within the stabilizer 200, which further lends itself to ease of application, as discussed in the preceding paragraph.

Because interferential current can be delivered using the four surface skin electrodes 108 and electro-medical device 110 in the configuration of FIGS. 1 and 2, another embodiment of the present invention includes applying pre-modulated interferential stimulation in combination with motor-level patterned muscle electrical stimulation to improve the effectiveness of the latter type of stimulation. In a single treatment session, the pre-modulated interferential stimulation is applied first followed by the application of motor-level patterned electrical muscle stimulation. Applying pre-modulated interferential stimulation followed by motor-level patterned electrical muscle stimulation improves the effectiveness of the motor-level patterned electrical muscle stimulation because of the interferential stimulation's ability to decrease a patient's sensitivity to higher intensities of motor-level patterned electrical muscle stimulation. And because the placement of the surface skin electrodes 108 is the same for both types of electrical stimulation of the present invention, the patient will not need to adjust or move the surface skin electrodes 108 or the stabilizer 200 to apply those different types of electrical stimulation.

It should be understood by one of ordinary skill that other alternative types of electrical stimulation can be used before and after the patterned muscle stimulation treatment to enhance effectiveness. Examples of different types of stimulation include, but are not limited to, Transcutaneous Electrical Nerve Stimulation (TENS), Interferential Stimulation, Diadynamic Stimulation, High Volt Galvanic Stimulation (HVGS), Electro-Magnetic and Pulsed Electro-Magnetic Field Stimulation (EMF & PEMF) and Micro-current Stimulation.

In any of the exemplary embodiments of the present invention, the duration of each type of stimulation may be from about 10 minutes to about 4 hours per day. Further, when interferential stimulation is applied at a sensory level, it may be applied in a range from 0.1 mA to 150 mA as rated into a 500 Ohm load. Interferential stimulation may also be applied with a resulting beat frequency between 0 and 250 Hz with a base frequency between 1 and 20 KHz. When motor-level stimulation is applied in a pattern based on a sequence of electromyographic output, it may be applied in a range from 5 mA to 150 mA as rated into a 500 Ohm load. That stimulation may be applied at a constant intensity from the beginning of the "on time" to the end of the "on time," with no stimulation being provided during the "off time." Or to provide smoother transitions between "off times" and "on times," stimulation may be ramped up to a specific intensity at the beginning of the "on time" and ramped back down to zero at the end of the "on time", as disclosed for example to U.S. Pat. Nos. 6,393,328 and 6,988,005 to McGraw et al., the disclosures of which are hereby incorporated by reference as if fully set forth herein.

Additionally, proper and reproducible placement of the surface skin electrodes 108 may be facilitated through the use of an applicator other than a stabilizer 200. Such applicators include compression units, slings, and other alternative garments that are designed to actively support weight-bearing articular segments 100 while allowing them to maintain their mobility. Like the stabilizer, such applicators are intended to allow the surface skin electrodes 108 to be positioned on the muscle groups 104 and 106 associated with the affected joint 102 in a manner reproducible each time it is worn by providing predetermined locations therein for positioning the surface skin electrodes 108. The predetermined locations correspond to the muscle groups 104 and 106 associated with the affected joint 102 around which the applicator is to be worn.

C. Examples

The present invention may be better understood with reference to the accompanying examples that are intended for purposes of illustration only and should not be construed to limit the scope of the invention, as defined by the claims appended hereto.

i. Example 1

Comparing the Benefits of Patterned Muscle Stimulation to TENS in the Treatment of Osteoarthritis of the Knee Degenerative joint disease and osteoarthritis are progressive disease processes that affect articular joints, including but not limited to, the hips, knees, ankles, toes, back, neck, and shoulders. Typically, the weight-bearing joints, such as the hips, knees and ankles are most affected by osteoarthritis. The most common type of arthritis is osteoarthritis of the knee. More than 10 million Americans suffer from osteoarthritis of the knee, with most of those affected being older than 45 years of age. Pathologic changes in degenerative joint disease and osteoarthritis involve the progressive breakdown of the articular cartilage matrix.

A total of 116 patients who qualified for inclusion in this investigation were enrolled in one of five medical centers in the United States. The patients were randomly placed into "test" and "sham-control" stimulation groups and blinded to their assignment. The clinicians too were blinded to the stimulation group assignment in order to allow them to act as independent observers and evaluators. The study was completed after the 8-week assessment with a total of 101 patients.

During this investigation, the test group received a daily 35 minute session of stimulation, which consisted of 15 minutes of pre-modulated interferential stimulation, followed by 20 minutes of motor-level patterned muscle stimulation. During the pre-modulated interferential stimulation, the patients were asked to increase the intensity of the stimulation until experiencing a gentle tingling feeling on the skin, but not muscular contraction. The pre-modulated interferential stimulation had a base frequency of 5000 Hz and a pre-modulated beat frequency sweeping between 1 and 150 Hz. After 15 minutes of pre-modulated interferential stimulation, motor-level patterned muscle electrical stimulation was applied to the test group. The stimulation was as triphasic stimulation pattern that included stimulating to the point of contraction, the quadriceps, hamstrings and quadriceps, in that specific order with periods of intermittent overlap. This pattern was based on an electromyographic output of the normal contraction patterns and timing of the quadriceps and hamstrings during a high-level running activity. Patients were instructed to increase the intensity of the motor-level stimulation until feeling a mild but comfortable muscular contraction, and after five minutes to turn up the intensity to produce a moderate to strong contraction that could be tolerated without causing pain. The motor-level patterned muscle stimulation delivered 50 Hz impulses for 200 milliseconds every 1500 milliseconds, while stimulation amplitude was fixed at 60 mA and patients controlled stimulation intensity by varying the pulse width, with intensity settings varying from 0.08 C to 11.38 C.

During each low-current TENS session for patients in the sham-control group, stimulation was delivered as a square wave with a 0.2 Hz frequency and a fixed amplitude of 60 mA, with pulse width adjusted to provide a net output of 73 nC. During the TENS stimulation, the patients were told that the stimulation might be perceived but would not produce a muscular contraction (i.e., that stimulation would be at a sensory level but not at a motor level). Patients receiving low-current TENS stimulation were also told that the intensity of the stimulation was preset and that adjustments had no effect on the actual current.

The primary efficacy criteria included the pain, physical function and stiffness subscales of the Western Ontario MacMaster (WOMAC) Osteoarthritis Index and Visual Analog Scales (VAS) for pain and quality of life. The WOMAC used in this study was the Likert version 3.1 standardized with English for an American population, consisting of 24 self-administrated questions that were answered for each item on a 5-point Likert scale (none, mild, moderate, severe and extreme). The 24 questions were reported under three separate subscales: pain, physical function, and stiffness. The pain subscale had five questions scored 0 to 4 and was considered invalid if more than one item was missing; hence, it had a range of 0 (no pain) to 20 (maximal pain). In the event of a missing item, the remaining four items were averaged and then multiplied by 5. The function subscale had 17 questions scored 0 to 4 and was considered invalid if more than three items were missing; hence, it had a range of 0 (maximal function) to 68 (minimal function). In the event of missing items, the remaining items were averaged and then multiplied by 17. The stiffness subscale had two items scored 0 to 4 and was considered invalid if either was missing; hence, it had a range from 0 (no stiffness) to 8 (maximal stiffness). In the event of a missing item, the score for remaining item was multiplied by 2.

VAS lines were used for measuring overall pain intensity and global impact of osteoarthritis on quality of life. The VAS line for overall pain rating was anchored at one end with a "0" and the label "No Pain" and at the other end with a "100" and the label "Worst Pain Imaginable." The VAS line for the quality of life rating was anchored at one end with a "0" and the label "Very Poor" and at the other end with a "100" and the label "Very Good." Patients were instructed to place a mark on the respective VAS lines to report the intensity or quality of the sensation being experienced. VAS ratings were provided for both knees.

Figure 5:
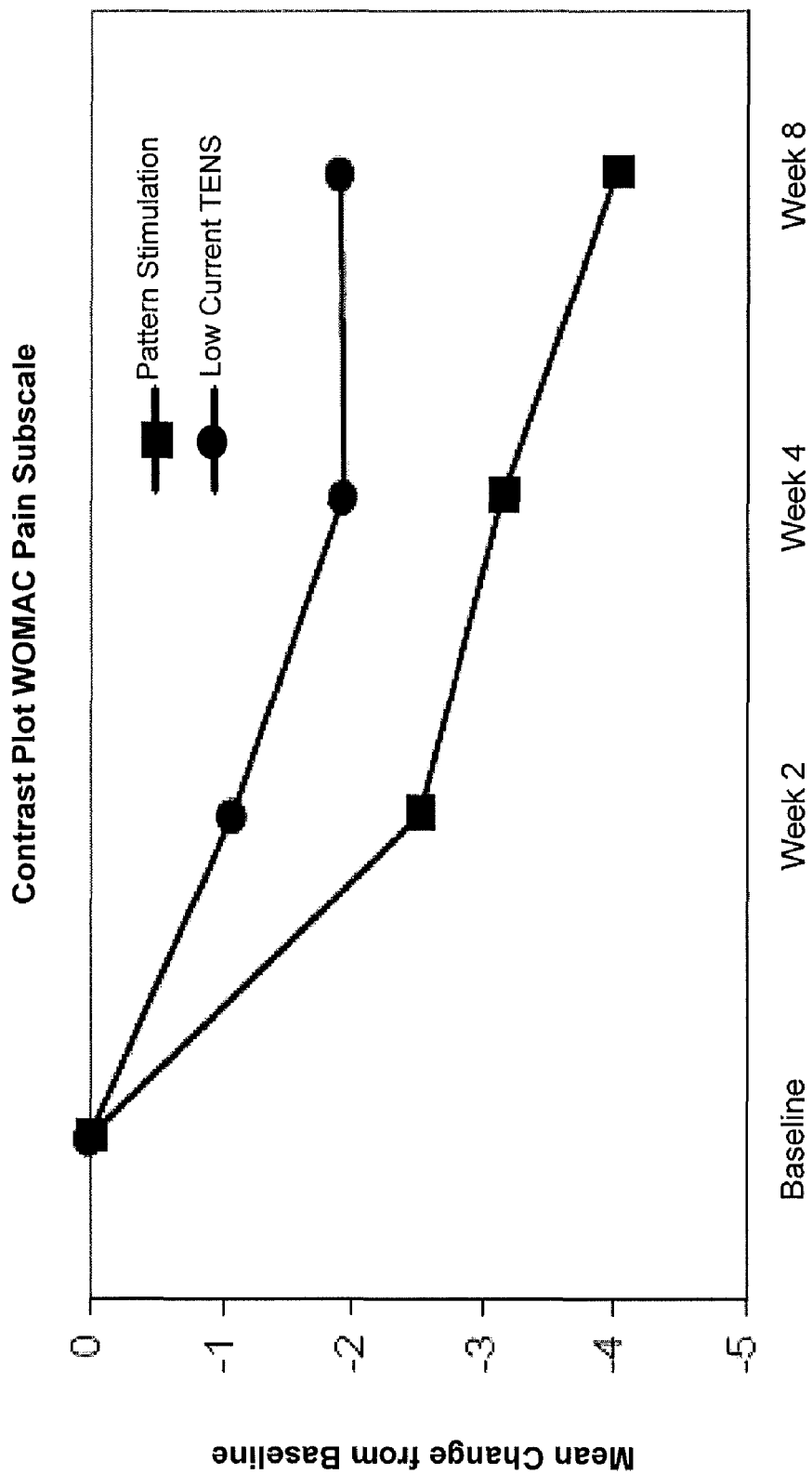
FIG. 5 is a contrast plot illustrating the WOMAC subscale of pain score in Example 1 of the present invention.
Figure 6:
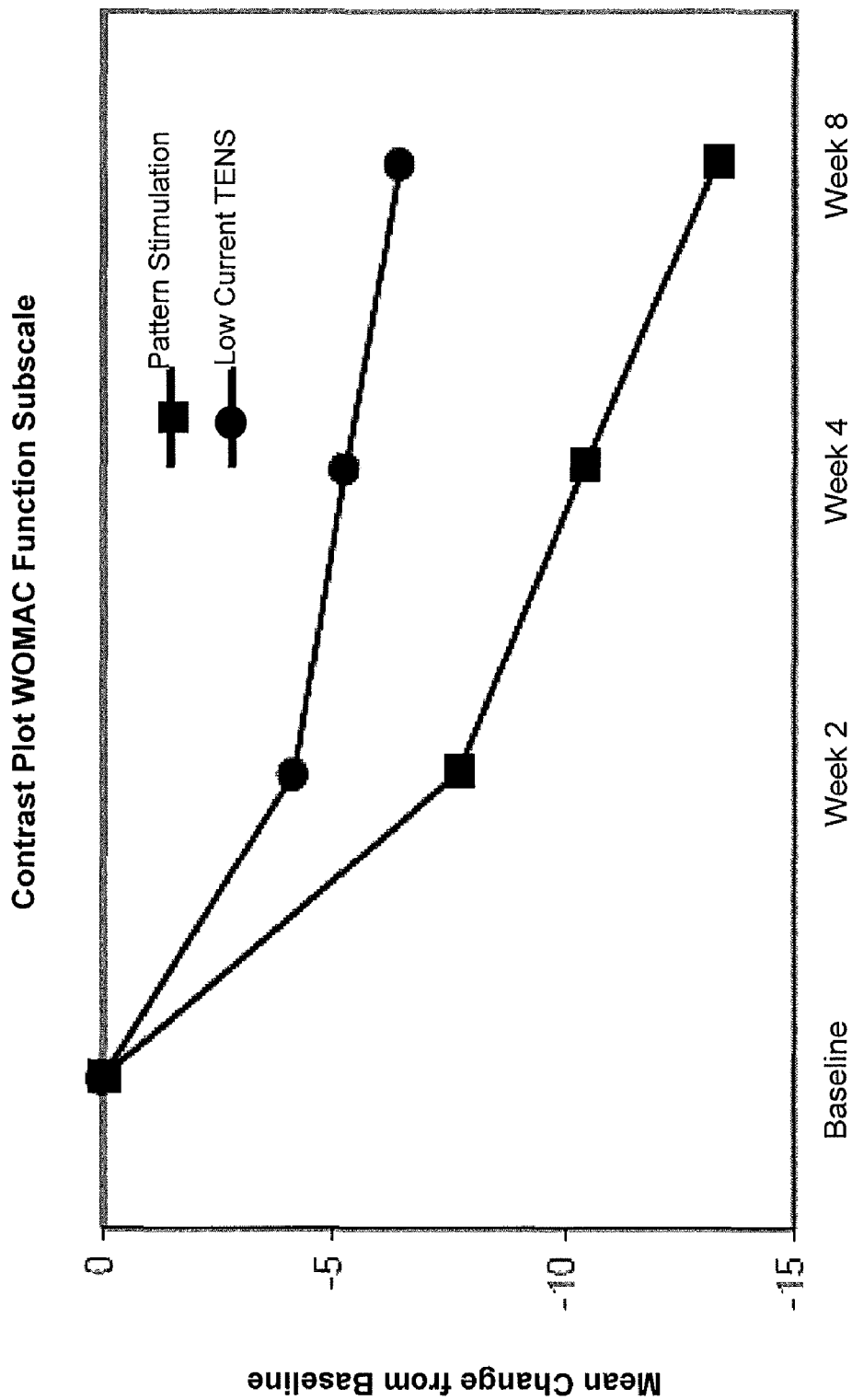
FIG. 6 is a contrast plot illustrating the WOMAC subscale of function score in Example 1 of the present invention.
Figure 7:
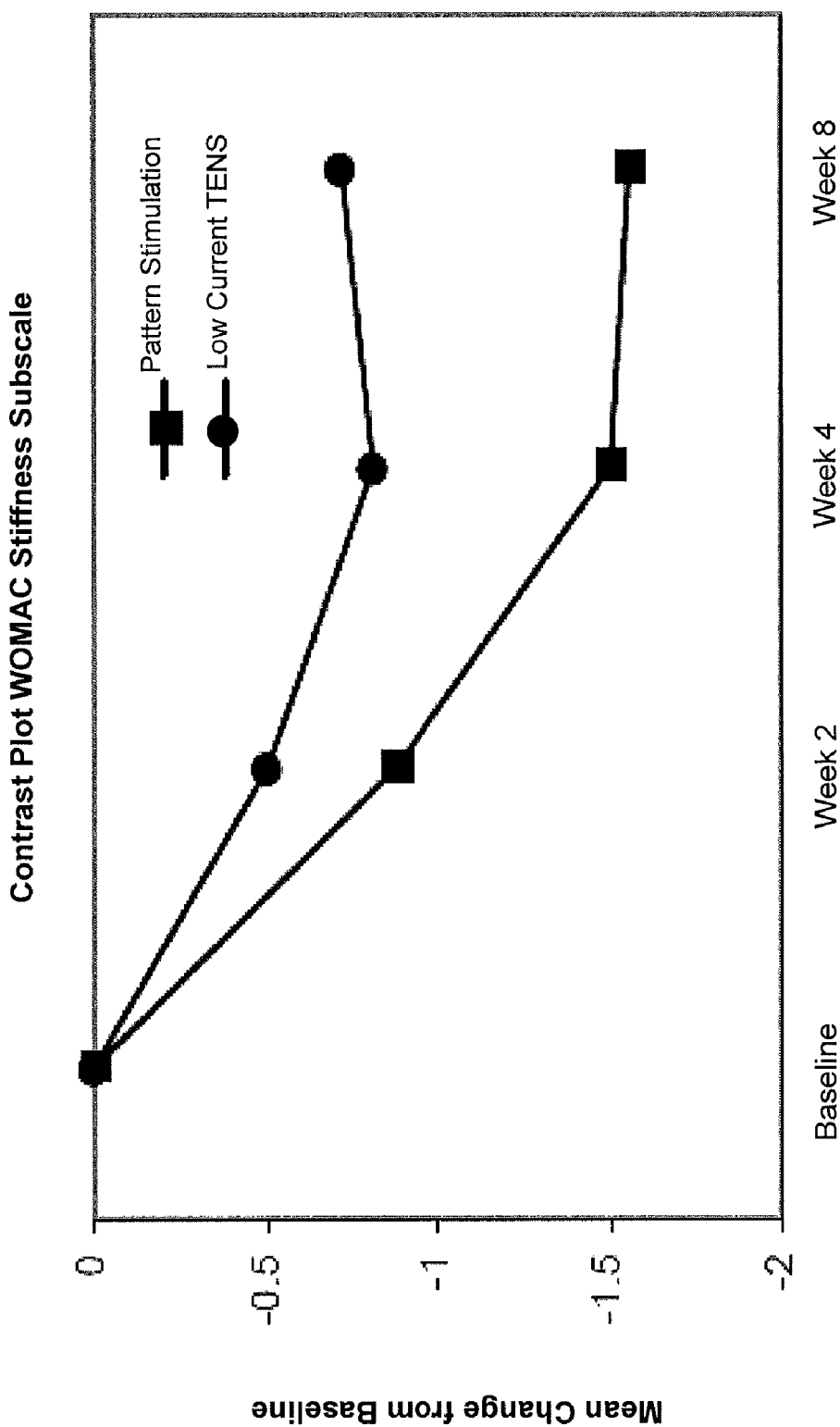
FIG. 7 is a contrast plot illustrating the WOMAC subscale of stiffness score in Example 1 of the present invention.

The scores based on the WOMAC and VAS efficacy criteria were expressed as a baseline mean value measured prior to the first stimulation session and a value of mean change from that baseline value measured in the subsequent eight weeks. A lower mean change from baseline was indicative of less impact on osteoarthritis. In the eight-week treatment data, statistically significant differences for each of the three WOMAC subscales favored the method of the present invention. Specifically, the test and sham-control groups had comparable baseline means for each of the three WOMAC subscales (P values>0.5). Patients in the test group had significantly greater reduction than patients in the sham-control group in the WOMAC pain subscale (3.98 vs. 1.90; P=0.002), physical function subscale (12.86 vs. 6.74; P=0.003), and stiffness subscale (1.53 vs. 0.74; P=0.004) after 8 weeks of treatment. FIG. 5 illustrates the contrast between test and sham-control groups in the WOMAC pain subscale at each scheduled visit; FIG. 6 illustrates the contrast between test and sham-control groups in the WOMAC physical function subscale at each scheduled visit; and FIG. 7 illustrates the contrast between test and sham-control groups in the WOMAC stiffness subscale at each scheduled visit. This data demonstrates that pre-modulated interferential stimulation followed by motor-level patterned muscle stimulation of the present invention is significantly more efficient than conventional low-current TENS in relieving pain, increasing function, and decreasing stiffness.

The WOMAC reduction values for each of the three subscales, when viewed as a percentage of each other within each subscale, further exemplify the superiority of pre-modulated interferential stimulation followed by motor-level patterned muscle stimulation over conventional low-current TENS. In the pain subscale for the test group, the reduction value (3.98) divided by the number of questions for the pain subscale (5) equals 80%. For the sham-control group the reduction value (1.90) divided by the number of questions for the pain subscale (5) equals 38%. As a percentage of each other, the test group percentage (80%) minus the sham-control group percentage (38%) divided by the sham-control group percentage (38%) equals 110%. This indicates that pain in the test group was 110% reduced to that in the sham-control group.

In the physical function (difficulty performing daily activities) subscale of WOMAC reduction values, the test group reduction value (12.86) divided by the number of questions for the difficulty performing daily activities subscale (17) equals 76%. For the sham-control group the reduction value (6.74) divided by the number of questions for the difficulty performing daily activities subscale (17) equals 40%. As a percentage of each other, the test group percentage (76%) minus the sham-control group percentage (40%) divided by the sham-control group percentage (40%) equals 90%. This indicates that difficulty performing daily activities in the test group was 90% reduced to that in the sham-control group.

In the stiffness subscale of WOMAC reduction values, the test group reduction value (1.53) divided by the number of questions for the stiffness subscale (2) equals 77%. For the sham-control group the reduction value (0.74) divided by the number of questions for the stiffness subscale (2) equals 37%. As a percentage of each other, the test group percentage (77%) minus the sham-control group percentage (37%) divided by the sham-control group percentage (37%) equals 108%. This indicates that stiffness in the test group was 108% reduced to that in the sham-control group.

Although the test and sham-control groups also had comparable baseline means for both VAS ratings, the mean changes from baseline to last visit in quality of life VAS rating were similar between the test and sham-control groups (18.17 vs. 18.16; P=0.99) while patients in the test group had a greater decrease in the overall pain VAS (27.91 vs. 23.19; P=0.29) after eight weeks of treatment. The difference between the overall pain VAS in the treatment groups, however, did not achieve statistical significance. On the other hand, if only patients who completed the study (49 in the test group and 50 in the sham-control group) were included in the analysis, the difference between groups in mean change from baseline increased from 4.71 to 9.40 for overall pain VAS rating and achieved statistical significance (P=0.038). While the collective data did not achieve a statistical difference in the overall pain VAS assessment, it was not expected that overall pain and quality of life VAS would achieve statistical significance. Unlike WOMAC, which is a test specifically designed for osteoarthritis of the knee, VAS assessment are tests for general purposes and less accurate in measuring osteoarthritis of the knee than WOMAC.

Additionally, two secondary effectiveness analyses, which included only patients who completed the study, were performed for the WOMAC pain and function scale. The first analysis assessed the interaction of treatment group by time. The mean change from baseline to each scheduled visit for the two treatment groups were contrasted. The results showed that at the Week 2 visit, patients in the test group already had significantly greater reduction in WOMAC subscales of pain (2.50 vs. 1.08; P=0.008) and function (7.74 vs. 4.14; P=0.03) than patients in the sham-control group. This result demonstrates that pre-modulated interferential stimulation followed by patterned muscle stimulation of the present invention has a beneficial effect after only two weeks of stimulation while conventional single-stage low-current TENS did not.

The other secondary effectiveness analysis compared the frequency of sham-control group and test group patients who reported 20% or more improvement in WOMAC scores in two post-baseline visits. The results of the comparison showed that a higher percentage of patients in the test group had improvement for WOMAC subscales of pain (71.2% vs. 49.1%; P=0.023) and function (65.4% vs. 45.3%; P=0.030) than patients in the sham-control group. Therefore, the results of the two secondary effectiveness analyses mirrored the primary analyses, favoring of the method of the present invention over single-stage low-current TENS.

The analysis of this carefully controlled clinical investigation provides scientific evidence that the method of the present invention is safe and effective for use in treating patients with osteoarthritis of the knee. Specifically, the results provide statistically significant evidence that the method of the present invention reduces pain in a knee joint affected with osteoarthritis. This statistically significant evidence was in the form of improvements on the WOMAC subscales of pain, physical function and stiffness.

ii. Example 2

The Effect of Sequential Electrical Stimulation on Osteoarthritis

An animal model was used for quantitative analyses of the components of synovial fluid that affect cartilage matrix degradation.

In an investigation on adult hound dogs, subjects were selected from dogs housed at Washington State University and under the care of personnel from the Comparative Orthopedic Research Laboratory (CORL). Each dog had a cartilage defect made previously and had established osteoarthritis in one of two stifle joints. Based on this criteria, a total of 11 adult hound dogs (six female and five male) were enrolled in the study.

The selected subjects, each being identified with a unique six-letter alphabetical identification tag, were randomly placed into "test" and "control" stimulation groups of five each, with one dog serving as the spare to replace a dog that might develop complications from surgery. Veterinary technicians placed the electrodes on both groups and applied stimulation to the test groups, with the technicians that took experimental measurements being blinded to the stimulation group assignment so as to allow them to act as independent observers and evaluators. The study interval was 12 weeks in length with the subjects in both groups receiving a single session of 30 minutes of treatment on a daily basis for six days per week during the 12-week period. The test group received 30 minutes of motor-level patterned muscle stimulation while the control group had the electrodes placed on them for 30 minutes without applying any electrical stimulation.

A single technician observed and recorded the subjects' pain on a VAS scale and measured the subjects' ground reaction forces using a force plate at baseline and on a weekly basis thereafter. Synovial fluid was collected from the affected joint of each subject at baseline and on a bi-weekly basis thereafter. Whenever synovial fluid was collected, 20 units of chymopapain were injected into the affected joint to maintain moderate lameness throughout degradation of the affected joint. Synovial fluid was collected only bi-weekly so that the weekly VAS scores and ground reaction force measurements could be evaluated for possible attenuation of lameness in the face of the chymopapain injections. This method of evaluation also made it possible to compare the synovial fluid data to the ground reaction force data at time points that matched that of the non-chymopapain weeks. In addition to this data, radiographs were taken of the affected joint at the beginning and end of the 12-week treatment. As a final source of data, a biopsy of osteochondral plug, i.e., bone or cartilage, was taken from each of the lateral and medial condyles in the affected body segment of each subject, both before and after the stimulation session.

The primary efficacy criteria for the ground reaction force data included Peak Vertical Force (PVF) and Vertical Impulse (VI). Ground reaction force data were recorded using a force plate capable of measuring stance time, propulsion impulse, breaking impulse, peak propulsion force, peak breaking force, peak vertical and vertical impulse forces. A pain score on a scale of 0 to 10 was used to measure overall pain. The pain score scale and criteria are adapted from a pain scoring system for evaluation of pain in dogs. (Can Vet J Volume 44, 2003 643-648).

Collected synovial fluid was assayed for sulfated glycosaminoglycans, hyaluronic acid, matrix metalloproteinase-3, albumin and soluble collagen. Due to a paucity of the synovial fluid collected from some of the subjects during the study, samples were group pooled to allow a large enough volume to run the analyses for the different synovial markers.

Biopsies of the osteochondral plugs were performed under general anesthesia and subjected to a histopathology evaluation. The evaluation focused on the condition of the articular cartilage and subchondral bone, and the severity of inflammation and fibrosis with a 0 to 4 semi-quantitative scoring system, with the higher score corresponding to a more prominent feature. The difficulty to consistently obtain osteochondral plugs from the medial and lateral condyle of the affected body segments, however, impacted the histopathological evaluation of the changes at tissue level. The histology sections prepared along the long axis of the biopsies sometimes showed no presence of articular cartilage (four of 18 in the control group and three of 22 in the test group). Therefore, the analyses focused on the trend of anatomical indices of improvement rather than statistics.

Improvements in anatomical indices were determined from the appearance of chondrocytes in the hypertrophic zone of the hyaline type articular cartilage using a Safranin O stain assay for determining the normal amounts of glycosaminoglycans. Articular cartilage has columns of chondrocytes arranged in an orderly fashion as layers of proliferative and hypertrophic chondrons without clustering, i.e., multiple chondrocytes in one chondron. Subchondral bone was distinguished from articular cartilage by observing that subchondral bone would have properly spaced trabeculae with appropriate thickness and marrow contents without inflammation and fibrosis. The stronger and closer the staining of the cartilage was to the color red, the greater the indication that the cartilage contained a normal amount of glycosaminoglycans.

The ground force reaction data were analyzed and expressed as a baseline mean value measured prior to the first stimulation session of Week 0 and a value of mean change from that baseline value measured in the subsequent 12 weeks. A greater percentage change from baseline was indicative of a positive response to the method of the present invention. In the 12-week treatment data, however, there was no significant percentage change from baseline in PVF or VI scores within each group over time, but there was a graphic trend for the test group to perform better than the control group after each week of stimulation sessions. Specifically, there was a major graphic trend for the test group to have a greater PVF and VI scores over the control group after each stimulation session, on both chymopapain injection weeks and non-chymopapain injection weeks. This data demonstrates that the motor-level patterned muscle stimulation of the present invention improves behavior indices such as PVF and VI in adult hound dogs with osteoarthritis as compared to adult hound dogs with osteoarthritis that receive no stimulation to their affected articular joints.

The weekly VAS scores were correlated with the corresponding weekly measurements of percent mean change of PVF and VI to evaluate a possible attenuation of lameness in the face of chymopapain on chymopapain injection weeks. There was a significant negative correlation between VAS scores and both PVF measurements (Pearson Correlation Coefficient=−0.70725, $p<0.0001$) and VI measurements (Pearson Correlation Coefficient=−0.70402, $p<0.0001$). This negative correlation demonstrates that where overall pain decreased in the test group, PVF and VI values increased. The low p-value demonstrates that the measurements taken on chymopapain injection weeks were consistent with those taken on non-chymopapain injection weeks.

The synovial fluid was analyzed for the presence of markers such as sulfated glycosaminoglycans, hyaluronic acid, matrix metalloproteinase-3, albumin and soluble collagen, with a decrease in the presence these markers being indicative of a positive response to the method of the present invention. In the 12-week treatment data, however, there was no significant change in the presence of the synovial fluid markers within each group over time, but there was a graphic trend for the test group to have less sulfated glycosaminoglycans, hyaluronic acid, and matrix metalloproteinase-3 in their synovial fluid than the control group after every two week period of stimulation sessions. In addition to there being a strong graphic trend for a positive effect in decreasing sulfated glycosaminoglycans, graphic trends confirmed a positive significance between the test group and control group at T12 ($p=0.0026$) for albumin concentrations and at T6 ($p=0.0001$), T10 ($p<0.0001$), and T12 ($p<0.0001$) for soluble collagen concentrations. The decrease in soluble collagen within the synovium was 20% compared to the control group. This data demonstrates that the motor-level patterned muscle stimulation of the present invention improves the quality of synovial fluid in adult hound dogs with osteoarthritis as compared to adult hound dogs with osteoarthritis that receive no stimulation to their affected body segments by reducing the amount of glycosaminoglycans, albumin and soluble collagen in synovial fluid.

For paired comparison between the pre-treatment and the post-treatment biopsies, three pairs from the control group and four pairs from the test group were used to measure anatomical indices of osteoarthritis. The severity of inflammation and fibrosis in the marrow and synovium between the pre-treatment and the post-treatment biopsies increased in the control group, while both parameters remained similar in the treated group (not statistically different). The subchondral bone showed mixed features of increased erosion by osteoclasts in some samples and compensatory sclerotic thickening of trabeculae in others. The pattern of change in the morphology of articular cartilage on the lateral condyle improved in the test group, from a negative average (degenerative) to a positive average (repairing), and deteriorated in the control group. The improvements were determined from the relatively normal appearance of chondrocytes in the hypertrophic zone of the hyaline type articular cartilage and the strong red staining of Safranin O for glycosaminoglycans. The subchondral bone of the lateral condyle in the test group seemed to have thickness and space near normal condition. The medial condyle of the test group, however, had similar morphological features in pre- and post-treatment conditions.

As illustrated in FIGS. 8A-9B, photomicrographs demonstrate the differences in pre- and post-treatment of the test and control and control groups. These histology slides were prepared from the biopsies through a process of decalcification in formic acid, dehydration and embedding in paraffin, staining with Safranin O and counter-staining with fast green. The cartilage appeared orange to red while bone appeared in light bluish green. Cellularity in the marrow represented the inflammatory infiltration, accompanied by fibrosis.

Figure 8A:
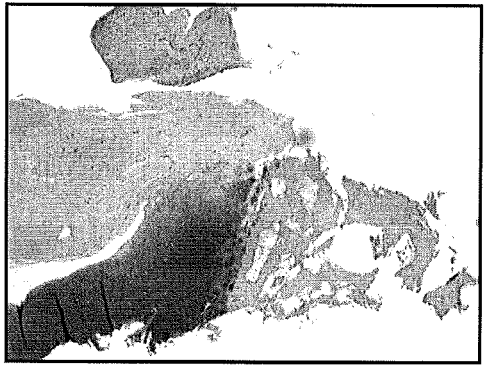
FIG. 8A is a photomicrograph illustrating a histology of a baseline biopsy of lateral condyle control group obtained in Example 2 of the present invention.
Figure 8B:
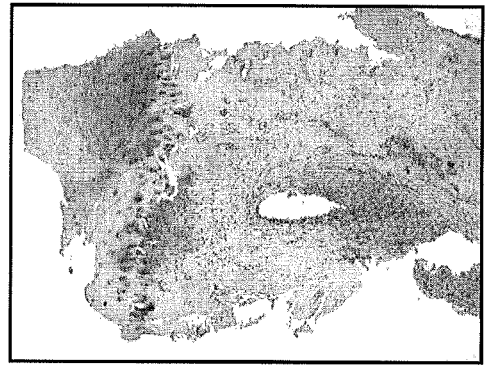
FIG. 8B is a photomicrograph illustrating a histology of a Week 12 biopsy of lateral condyle control group obtained in Example 2 of the present invention.
Figure 9A:
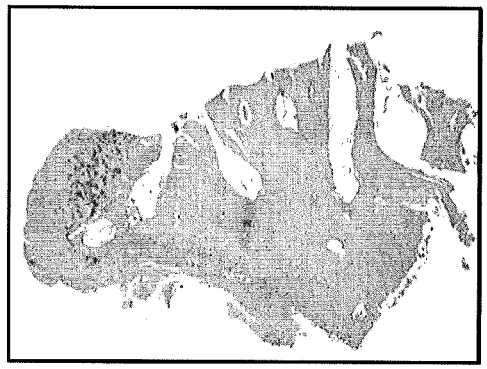
FIG. 9A is a photomicrograph illustrating a histology of a baseline biopsy of lateral condyle test group obtained in Example 2 of the present invention.
Figure 9B:
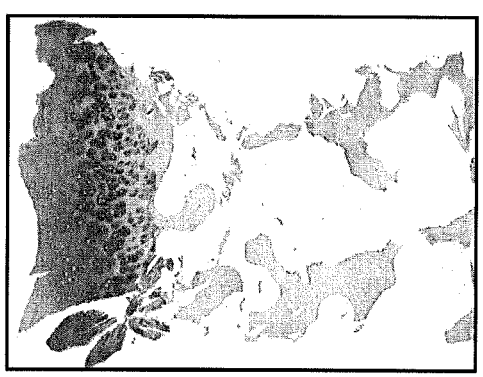
FIG. 9B is a photomicrograph illustrating a histology of a Week 12 biopsy of lateral condyle test group obtained in Example 2 of the present invention.

FIG. 8A illustrates a photomicrograph from a control group biopsy at baseline and FIG. 8B illustrates the corresponding photomicrograph from a biopsy from the same control group subject after Week 12. FIG. 9A illustrates a photomicrograph from a test group biopsy at baseline and FIG. 9B illustrates the corresponding photomicrograph from a biopsy from the same test group subject after Week 12. FIG. 8B illustrates a decrease in cartilage from FIG. 8A as indicated by a decrease in the amount of orange and red shown in FIG. 8B, Comparatively, FIG. 9B illustrates an increase in cartilage from FIG. 9A as indicated by an increase in the amount of orange and red shown in FIG. 9B. FIGS. 8A-9B therefore provide evidence that the pattern of change in the morphology of articular cartilage on the lateral condyle improved in the test group from a negative average to a positive average while it deteriorated in the control group.

The analysis of this carefully controlled investigation provides valid scientific evidence that the method of the present invention improves the quality of synovium fluid. Specifically, the results provide evidence that applying motor-level patterned muscle stimulation based on an electromyographic output of normal musculature activation-timing and sequential patterning decreases albumin and soluble collagen concentrations within the synovium fluid of the animal models' affected joints. The improvement indicates that matrix degradation from articular cartilage is attenuated in this osteoarthritis model. As compared to the control group, graphic trends of the synovial markers, ground reaction force data and the histopathological improvements support a positive effect on the clinical osteoarthritis condition of the subjects that underwent treatment per the method of the present invention. The results demonstrate the effectiveness of the present invention in treating established osteoarthritis by reducing the amount of glycosaminoglycans, albumin and soluble collagen in synovial fluid.

As demonstrated by the two Examples, methods and apparatus according to the non-limiting aspects of the present invention increase the mobility of weight-bearing articular joints that are affected by osteoarthritis, as well as control the progressive process cartilage matrix degradation. Statistically significant improvement in efficacy criterion measuring change in terms of WOMAC subscales of pain, function and stiffness support this conclusion. Graphic trends demonstrating decreases in glycosaminoglycans, and statistically significant less amounts of albumin and soluble collagen in synovial fluid also support this conclusion, providing physical indicia that establish the present invention's ability to improve the quality of synovial fluid. The clinical studies therefore provide scientific evidence that the present invention is an effective method for decreasing the progressive process of joint deterioration.

D. Summary

As demonstrated by the preceding examples, the apparatus and method of the present invention overcome the shortcomings of the prior art by utilizing motor-level patterned electrical muscle stimulation in combination with a stabilizer to improve mobility of and to control cartilage matrix degradation in affected, weight-bearing, articular joints. For example, the electrical stimulation of Cywinski is applied at an intensity far below the stimulation rate necessary to achieve fused and forceful contraction of muscle while the electrical stimulation of Aleev is applied at an intensity that causes the articular segment 100 to actually move through its full range of motion. The former is not sufficient to naturally enhance the vegetative function of the affected joint 102 while the latter results in the type of grinding and friction that actually contribute to cartilage matrix degradation.

Similarly, the electrical stimulation of Shiba is applied while a patient is moving his or her articular segment 100 through its full range of motion, which also results in the type of grinding and friction that contribute to cartilage matrix degradation. And rather than stimulating multiple muscle groups in a pattern to cause the articular segment 100 to move through its full range of motion, the electrical stimulation of Shiba is applied to a single antagonist muscle as the patient cognitively causes the articular segment 100 to move through its full range of motion by actively contracting the corresponding agonist muscle. Accordingly, the electrical stimulation of Shiba is not applied at a motor level (i.e., higher than a sensory level but lower than a level that would cause the articular segment 100 to actually move through its full range of motion) nor does it mimic a pattern of normal joint action. Moreover, the resulting muscle contractions subject the affected joint 102 of that articular segment 100 to compressive axial loading, which runs counter to controlling cartilage matrix degradation. Accordingly, the prior art fails where the present invention succeeds.

The present invention may be embodied in other forms or carried out in other ways without departing from the spirit or essential characteristics thereof. For example, although the stabilizer 200 of the preferred embodiment is described as a single-hinge device, it may also be a double-hinge device without departing from the spirit or essential characteristics of the present invention. The present disclosure and enumerated examples are therefore to be considered as in all respects illustrative and not restrictive, the scope of the invention being indicated by the appended claims, an all equivalency are intended to be embraced therein. One of ordinary skill in the art would be able to recognize equivalent embodiments of the instant invention and be able to practice such embodiments using the teaching of the instant disclosure and only routine experimentation.

What is claimed is:

1. A method for improving mobility of an affected joint of an articular segment, wherein the joint is associated with at least a first muscle group and at least a second muscle group each having an antagonistic relationship for causing the articular segment to move through a range of motion when recruited by natural neural impulses, the method comprising:
    positioning at least two first electrodes proximate to the at least first muscle group;
    positioning at least two second electrodes proximate to the at least second muscle group;
    placing an applicator on the articular segment such that the at least two first electrodes and the at least two second electrodes are disposed between the applicator and the articular segment, the applicator being configured to reduce compressive forces on at least one compartment of the affected joint; and
    applying motor-level electrical stimulation to the at least first and second muscle groups via the at least two first and second electrodes in a multiphasic pattern corresponding to a sequence of electromyographic outputs.

2. The method of claim 1, further comprising the step of removably attaching the at least two first electrodes and the at least two second electrodes to the applicator such that the step of placing the applicator on the articular segment performs the steps of positioning the at least two first electrodes and the at least two second electrodes proximate to the at least first muscle group and the at least second muscle group, respectively.

3. The method of claim 1, further comprising the step of applying a torque to the articular segment with the applicator.

4. The method of claim 1, further comprising the steps of:
    electrically connecting the at least two first electrodes to a first channel of an electro-medical device as a first anode-cathode pair; and
    electrically connecting the at least two second electrodes to a second channel of the electro-medical device as a second anode-cathode pair,
    wherein the multiphasic pattern of motor-level electrical stimulation is generated with the electro-medical device.

5. The method of claim 1, wherein
    said affected joint is a knee joint of a human body; and
    said applicator is a brace that envelopes the knee joint and provides medial and lateral thrusts to oppose at least one pathologically unbalanced load within the at least one compartment of the knee joint.

6. The method of claim 5, wherein the step of positioning the at least two first electrodes includes positioning such electrodes at a front area of a thigh and the step of positioning the at least two second electrodes includes positioning such electrodes at a back area of the thigh.

7. The method of claim 1, wherein the step of applying the motor-level electrical stimulation includes applying the motor-level electrical stimulation while the joint is in a position to minimize at least one of pressure and moving friction in the joint such that the weight-bearing load and moving friction of the joint is contemporaneously minimized during the step of applying the motor-level electrical stimulation.

8. The method of claim 1, wherein the sequence of electromyographic outputs corresponds to a pattern of electromyographic outputs recorded from antagonistic muscle groups recruited by natural neural impulses as those antagonistic muscle groups cause their respective articular segment to move through its full range of motion.

9. The method of claim 1, wherein the step of applying motor-level electrical stimulation is preceded by a step of applying at least one of interferential stimulation, transcutaneous electrical nerve stimulation, high volt galvanic stimulation, or micro-current stimulation.

10. The method of claim 9, wherein the step of applying motor-level electrical stimulation is preceded by a step of applying interferential stimulation, wherein the interferential stimulation is sensory-level pre-modulated interferential electrical stimulation.

11. The method of claim 10, wherein the step of applying interferential stimulation includes:
    applying a first frequency of electrical stimulation via the at least two first electrodes; and
    applying a second frequency of electrical stimulation via the at least two second electrodes;
    wherein said second frequency has an interference relationship with said first frequency to produce at least one beat frequency.

12. The method of claim 1, wherein the step of applying motor-level electrical stimulation in a multiphasic pattern includes:
    beginning a first phase of applying motor-level electrical stimulation to the at least first muscle group and ending the first phase of applying;

beginning a second phase of applying motor-level electrical stimulation to the at least second muscle group before ending the first phase of applying and ending the second phase of applying after ending the first phase of applying;

beginning a third phase of applying motor-level electrical stimulation to the at least first muscle group before ending the second phase applying and stopping the third phase of applying; and repeating the first phase of applying, the second phase of applying, and the third phase of applying.

13. The method of claim 12, wherein the step of applying motor-level electrical stimulation in a multiphasic pattern includes applying the stimulation in an amount effective for controlling at least one cartilage matrix degradation marker selected from a group consisting of sulfated glycosaminoglycans, albumin, and soluble collagen.

14. An apparatus for improving mobility of an affected joint of an articular segment, wherein the joint is associated with at least a first muscle group and at least a second muscle group each having an antagonistic relationship for effecting mobility of the joint through a range of motion when recruited by natural neural impulses, the system comprising:

an electro-medical device configured to apply motor-level electrical stimulation in a multiphasic pattern via at least a first channel and at least a second channel, the multiphasic pattern being programmed into the electro-medical device and corresponding to the sequence of an electromyographic output for the joint;

at least two first electrodes connected to the at least first channel of said electro-medical device, the at least two first electrodes being positioned proximate to the at least first muscle group;

at least two second electrodes connected to the at least second channel of said electro-medical device, the at least two second electrodes being positioned proximate to the at least second muscle group; and an applicator configured to be worn on the articular segment such that the at least two first electrodes and the at least two second electrodes are disposed between the applicator and the articular segment, the applicator being further configured to reduce compressive forces on at least one compartment of the affected joint.

15. The apparatus of claim 14, wherein the applicator is further configured to removably receive the at least two first electrodes and the at least two second electrodes such that the at least two first electrodes and the at least two second electrodes are positioned proximate to the at least first muscle group and the at least second muscle group, respectively, when the applicator is worn on the articular segment.

16. The apparatus of claim 14, wherein the applicator is further configured to apply a torque to the articular segment.

17. The apparatus of claim 14, wherein said at least two first electrodes and said at least two second electrodes are connected to said electro-medical device such that said at least two first electrodes form a first circuit that operates with a first frequency and said at least two second electrodes form a second circuit that operates with a second frequency; and said electro-medical device is configured to apply the second frequency with an interference relationship with said first frequency to produce at least one beat frequency.

18. The apparatus of claim 14, wherein said affected joint is a knee joint of a human body; and said applicator is a brace that envelopes the knee joint and provides medial and lateral thrusts to oppose at least one pathologically unbalanced load within the at least one compartment of the knee joint.

19. The apparatus of claim 18, wherein the applicator is further configured to removably receive the at least two first electrodes and the at least two second electrodes such that the at least two first electrodes are positioned at a front area of a thigh and the at least two second electrodes are positioned at a back area of the thigh when the applicator is worn on the articular segment.

20. The apparatus of claim 14, wherein the joint is in a position to minimize at least one of pressure and moving friction in the joint such that the weight-bearing load and moving friction of the joint is contemporaneously minimized during the step of applying the motor-level electrical stimulation.

21. The apparatus of claim 14, wherein the sequence of electromyographic outputs corresponds to a pattern of electromyographic outputs recorded from antagonistic muscle groups recruited by natural neural impulses as those antagonistic muscle groups cause their respective articular segment to move through its full range of motion.

22. The apparatus of claim 14, wherein the electro-medical device is further configured to apply at least one of interferential stimulation, transcutaneous electrical nerve stimulation, high volt galvanic stimulation, or micro-current stimulation before and/or after the motor-level electrical stimulation.

23. The apparatus of claim 22, wherein the electro-medical device is further configured to apply interferential stimulation; and the interferential stimulation is sensory-level pre-modulated interferential electrical stimulation.

24. The apparatus of claim 22, wherein said electro-medical device is configured to apply interferential by applying a first frequency of electrical stimulation via the at least two first electrodes and applying a second frequency of electrical stimulation via the at least two second electrodes; and said second frequency has an interference relationship with said first frequency to produce at least one beat frequency.

25. The apparatus of claim 14, wherein the multiphasic pattern programmed into the electro-medical device includes:

beginning a first phase of applying motor-level electrical stimulation to the at least first muscle group and ending the first phase of applying;

beginning a second phase of applying motor-level electrical stimulation to the at least second muscle group before ending the first phase of applying and ending the second phase of applying after ending the first phase of applying;

beginning a third phase of applying motor-level electrical stimulation to the at least first muscle group before ending the second phase applying and stopping the third phase of applying; and repeating the first phase of applying, the second phase of applying, and the third phase of applying.

26. The apparatus of claim 25, wherein the electro-medical device is configured to apply motor-level electrical stimulation in a multiphasic pattern in an amount effective for controlling at least one cartilage matrix degradation marker selected from a group consisting of sulfated glycosaminoglycans, albumin, and soluble collagen.

* * * * *